United States Patent
Allred et al.

(10) Patent No.: US 7,172,423 B2
(45) Date of Patent: *Feb. 6, 2007

(54) SUBSTANTIALLY SOLID BLEACHING OR TREATMENT COMPOSITIONS IN THE FORM OF INSERTS FOR DENTAL TRAYS, AND KITS COMPRISING SUCH INSERTS AND TRAYS

(75) Inventors: Peter M. Allred, Riverton, UT (US); Dan E. Fischer, Sandy, UT (US); Neil T. Jessop, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 246 days.

This patent is subject to a terminal disclaimer.

(21) Appl. No.: 10/888,041

(22) Filed: Jul. 9, 2004

(65) Prior Publication Data

US 2004/0265245 A1 Dec. 30, 2004

Related U.S. Application Data

(63) Continuation-in-part of application No. 10/446,235, filed on May 27, 2003, now Pat. No. 7,074,042, and a continuation-in-part of application No. 10/446,471, filed on May 27, 2003, now Pat. No. 7,048,543, and a continuation-in-part of application No. 10/637,237, filed on Aug. 8, 2003, now Pat. No. 7,059,857, and a continuation-in-part of application No. 10/646,484, filed on Aug. 22, 2003, now Pat. No. 7,056,118, and a continuation-in-part of application No. 10/692,117, filed on Oct. 22, 2003, now Pat. No. 7,011,523.

(51) Int. Cl.
*A61C 15/00* (2006.01)
*A61K 9/20* (2006.01)

(52) U.S. Cl. .................. 433/216; 433/215; 424/53

(58) Field of Classification Search ............. 433/80, 433/215, 216; 424/53
See application file for complete search history.

(56) References Cited

U.S. PATENT DOCUMENTS

| | | | | |
|---|---|---|---|---|
| 4,764,377 | A | * 8/1988 | Goodson | 424/435 |
| 5,460,527 | A | 10/1995 | Kittelsen | 433/215 |
| 5,746,598 | A | 5/1998 | Fischer | 433/216 |
| 5,980,249 | A | 11/1999 | Fontenot | 433/80 |
| 5,985,249 | A | 11/1999 | Fischer | 424/49 |
| 6,036,943 | A | 3/2000 | Fischer | 424/49 |
| 6,126,443 | A | 10/2000 | Burgio | 433/215 |
| 6,274,122 | B1 | 8/2001 | McLaughlin | 424/53 |
| 6,306,370 | B1 | 10/2001 | Jensen et al. | 424/49 |
| 6,309,625 | B1 | 10/2001 | Jensen et al. | 424/49 |
| 6,364,665 | B1 | 4/2002 | Trettenero | 433/215 |

(Continued)

*Primary Examiner*—Todd E. Manahan
(74) *Attorney, Agent, or Firm*—Workman Nydegger

(57) ABSTRACT

Substantially solid dental bleaching or treatment compositions in the form of an insert for placement within a dental tray. The compositions comprise a substantially solid dental bleaching composition that has increased adhesiveness to teeth when moistened with saliva or water. The inserts are horseshoe shaped and may be either flat or contoured. The substantially solid dental bleaching composition becomes more adhesive when moistened with saliva or water, yet remains intact and coherent after the dental bleaching composition is placed within a dental tray and over a person's teeth during bleaching (or other treatment).

24 Claims, 8 Drawing Sheets

U.S. PATENT DOCUMENTS

| | | |
|---|---|---|
| 6,368,576 B1 | 4/2002 | Jensen et al. ............... 424/49 |
| 6,409,993 B1 | 6/2002 | Jensen et al. ............... 424/53 |
| 6,500,408 B2 | 12/2002 | Chen ........................ 424/53 |
| 6,514,484 B2 * | 2/2003 | Rajaiah et al. ............. 424/53 |
| 6,607,382 B1 * | 8/2003 | Kuo et al. .................. 433/6 |
| 6,638,496 B2 | 10/2003 | McLaughlin ............... 424/53 |
| 6,685,923 B2 | 2/2004 | Peterson et al. ........... 424/53 |
| 6,730,316 B2 | 5/2004 | Chen ........................ 424/435 |
| 2002/0081555 A1 * | 6/2002 | Wiesel ....................... 433/215 |
| 2002/0141950 A1 | 10/2002 | Chen ........................ 424/53 |
| 2002/0155070 A1 | 10/2002 | Chen ........................ 424/53 |
| 2003/0012746 A1 | 1/2003 | Chen ........................ 424/53 |
| 2003/0044361 A1 | 3/2003 | Chen ........................ 424/53 |
| 2003/0194383 A1 | 10/2003 | Gentile et al. ............. 424/53 |
| 2004/0005277 A1 * | 1/2004 | Willison et al. ........... 424/53 |
| 2004/0062724 A1 | 4/2004 | Moro et al. ................ 424/53 |

* cited by examiner

SUBSTANTIALLY SOLID BLEACHING OR TREATMENT COMPOSITIONS IN THE FORM OF INSERTS FOR DENTAL TRAYS, AND KITS COMPRISING SUCH INSERTS AND TRAYS

CROSS REFERENCE TO RELATED APPLICATIONS

This application is a continuation-in-part of U.S. application Ser. No. 10/446,235, filed May 27, 2003 now U.S. Pat. No. 7,074,042, and a continuation-in-part of U.S. application Ser. No. 10/446,471, filed May 27, 2003 now U.S. Pat. No. 7,048,543, and a continuation-in-part of U.S. application Ser. No. 10/637,237, filed Aug. 8, 2003 now U.S Pat. No. 7,059,857, and a continuation-in-part of U.S. application Ser. No. 10/646,484, filed Aug. 22, 2003 now U.S. Pat. No. 7,056,118, and a continuation-in-part of U.S. application Ser. No. 10/692,117, filed Oct. 22, 2003 now U.S. Pat. No. 7,011,523. The foregoing applications are incorporated herein in their entirety.

BACKGROUND OF THE INVENTION

1. The Field of the Invention

The present invention is in the field of dental bleaching devices used to bleach a person's teeth. More particularly, the invention relates to a substantially solid dental bleaching composition in the form of an insert for a dental tray.

2. The Relevant Technology

Virtually all people desire white or whiter teeth. To achieve this goal, people either have veneers placed over their teeth or have their teeth chemically bleached. In the past, patients who desired to have their teeth bleached had to submit to conventional in-office bleaching techniques. The process generally involves: (1) making an alginate impression of the patient's teeth; (2) making a stone cast or model of the impression; (3) vacuum forming a dental tray from the model, usually from a heated sheet of thin ethyl vinyl acetate (EVA) material, and (4) trimming to exclude gingival coverage. This method results in a tray that is soft and flexible, that is customized to very accurately fit over the patient's teeth, and that is therefore very comfortable to wear. However, the process for making a customized tray is time consuming, often taking days or weeks before the customized tray is available to the patient, and the resulting tray can be expensive.

Because of the time and cost associated with customized trays, less time consuming and costly alternatives have been developed. Contrary to marketing campaigns, however, many alternatives have substantial disadvantages, primarily in terms of their effectiveness (or ineffectiveness) in actually bleaching teeth. They also have their own unique issues relating to ease of use, comfort and poor taste (bleaching compositions are, after all, placed directly into a person's mouth).

One alternative to customized dental trays are non-customized trays that approximate the shapes and sizes of a variety of users' dental arches. While non-customized dental trays can be used without the need for a professional customization procedure by a dentist, such trays tend to be more bulky and less comfortable than custom-fitted trays. Dental trays that can be self-customized (e.g., so-called "boil and bite" trays) are somewhat more comfortable and better-fitting compared to non-custom trays but less comfortable than trays that are customized by a dentist.

Another alternative tooth bleaching method involves painting a bleaching composition directly onto the surfaces of a person's teeth to be bleached. An advantage of this procedure is that it eliminates the need to obtain a customized tray, or even a non-custom tray. The main disadvantage, however, is that the bleaching composition remains directly exposed to the person's saliva and disruptive forces and movements normally found within a person's mouth. The result is that a significant portion of the bleaching composition does not remain on the tooth where bleaching is desired. Instead, some or all of the composition can dissolve away into the person's saliva and/or be transferred to adjacent oral tissues. Because paint-on dental bleaching compositions, like all dental bleaching compositions, contain peroxide-based bleaching agents, irritation to soft oral tissues within the user's mouth and throat is a potential problem when using such compositions.

Yet another alternative tooth bleaching method involves placing a flexible bleaching strip over a user's tooth surfaces. Bleaching strips typically comprise a flexible plastic strip coated with a moist dental bleaching gel on the side of the strip facing the user's teeth. To install the bleaching strip, a portion of the bleaching strip is first placed over the front surfaces of the user's teeth, followed by folding the remainder of the strip around the occlusal edges of the teeth and back against a portion of the lingual surfaces. Like paint-on bleaching compositions, this procedure does not require the user to obtain a customized tray, or even a non-custom tray, into which a bleaching composition must be placed by the user prior to use. An advantage of bleaching strips over paint-on bleaching compositions is that bleaching strips include a barrier that, at least in theory, protects the dental bleaching gel from diffusing into the user's mouth.

In reality, however, because of the generally poor adhesion of bleaching strips to the user's teeth, coupled with their generally flimsy nature, it is often difficult for the user to maintain the bleaching strips in their proper position. Bleaching strips are prone to slip off the teeth through even minimal movement of the user's mouth, jaw or tongue. Indeed, it is recommended that the user not eat, drink, smoke or sleep while wearing the bleaching strip. In practice, it is difficult to talk while maintaining the bleaching strips properly oriented over the teeth to be bleached.

Even if a user successfully maintains the bleaching strip in its proper position during the entire bleaching event, the flowable bleaching gel can diffuse into the person's saliva, potentially causing a poor taste in the user's mouth and possibly discomfort to soft oral and throat tissues. The tendency of the bleaching gel to diffuse into the user's mouth can be accelerated through even minimal shifts of the bleaching strip over the user's teeth, with each shift potentially exposing a new portion of the bleaching gel that remains adhered to the newly exposed surface of the user's teeth. In some cases, the bleaching strip can become so dislodged or mangled that it must be removed by the user and replaced with a fresh bleaching strip to complete the recommended bleaching time. This multiplies the cost and hassle of the bleaching strip method.

In practical terms, the use of bleaching strips can greatly inhibit even the simplest of activities that involve movement of the user's mouth or tongue, such as talking, smiling, making other facial expressions, or even swallowing (which normally occurs subconsciously throughout the day). Indeed, the time when a person's mouth and tongue are prone to move the least is at night while the person is sleeping. Unfortunately, it is recommended that bleaching strips not be used while sleeping, presumably to prevent accidental choking on an inadvertently dislodged bleaching strip. This only confirms the tendency of such bleaching strips to easily dislodge from a user's teeth.

Ultimately, the main impediment to successful bleaching is the failure of users to complete the prescribed bleaching regimen. If the bleaching apparatus is difficult to use, requires numerous repetitions to achieve observable results, or is simply uncomfortable or a hassle to wear, the user may simply give up and abort the bleaching process altogether. Thus, even if significant dental bleaching is possible using a particular bleaching product, it is less likely to occur where the inadequacies of the bleaching apparatus or method causes users to become discouraged before desired results are attained.

In view of the foregoing, there is an ongoing need for improved bleaching apparatus and methods that are simple and easy to use, that more reliably remain in position over the user's teeth, and that result in less diffusion of bleaching composition into a user's oral cavity. Such improvements would be expected to improve or encourage compliance by the user.

BRIEF SUMMARY OF THE PREFFERED EMBODIMENTS

The present invention generally relates to substantially solid dental bleaching or other treatment compositions used to bleach or otherwise treat a person's teeth. Briefly summarized, the inventive dental compositions are substantially solid and in the form of an insert suitable for placement within a dental tray. The substantially solid dental treatment composition becomes more adhesive to teeth when moistened (e.g., by saliva or water). When inserted within a dental tray and placed over a person's teeth, the dental treatment composition reliably adheres to the teeth, maintaining contact between the teeth to be treated and a bleaching or other treatment agent within the treatment composition.

The bleaching or other treatment composition comprises a substantially solid, coherent dental treatment composition, as opposed to a liquid, gel, or dry particulate or powdery composition. As such, the substantially solid composition does not run or flow. Compared to bleaching gels, the substantially solid and coherent treatment composition better adheres to a person's teeth and does not readily diffuse into the surrounding oral cavity on its own, absent becoming diluted by saliva or moisture in a person's mouth. This, in turn, promotes better tooth whitening (or other treatment) and patient compliance.

The substantially solid dental treatment compositions according to the invention include at least one dental bleaching or other treatment agent and at least one oral tissue adhesion agent. Preferred dental bleaching agents include solid complexes of hydrogen peroxide. Non-limiting examples of dental bleaching agents that are a solid complex of hydrogen peroxide are carbamide peroxide and sodium perborate, although it is within the scope of the invention to use other dental bleaching agents known in the art.

In one embodiment, the oral tissue adhesion agent advantageously remains substantially non-adhesive when the dental treatment composition is in a dry or substantially solid condition but becomes adhesive to oral tissue (e.g., teeth) when the composition is moistened with, e.g., water or saliva. A non-limiting example of a suitable oral tissue adhesion agent is polyvinyl pyrrolidone (PVP), although it is within the scope of the invention to use other tooth adhesion agents known in the art.

The dental treatment composition may include other components as desired to yield a final composition having desired properties. Examples of other components include, but are not limited to, plasticizers and humectants (e.g., glycerin, sorbitol, and polyethylene glycol), volatile solvents (e.g., water and alcohols), stabilizing agents (e.g., EDTA), neutralizing agents, thickening agents (e.g., fumed silica), flavorants, sweeteners, and the like. Instead of or in addition to a dental bleaching agent, the treatment composition may include desensitizing agents (e.g., potassium nitrate), remineralizing agents (e.g., sodium fluoride or other fluoride salts), antimicrobial agents (e.g., chlorhexidine), antiplaque agents, anti-tartar agents, or other medicaments.

According to one embodiment, the dental treatment composition is made by first forming a flowable liquid or gel composition that is later subsequently dried to form a substantially solid treatment layer. This may be performed by heating or otherwise causing one or more volatile solvents to be driven off by evaporation, thus leaving behind a substantially solid treatment composition.

According to one embodiment, dental treatment compositions in the form of an insert according to the invention can be made by spreading a flowable dental treatment composition onto the surface of a large or continuous polymeric sheet. The polymeric sheet and treatment composition are then heated, such as in a forced air oven, to drive off a substantial portion of the water or other solvent that was used to form the flowable dental treatment composition in order to yield a substantially solid layer of bleaching or other treatment composition. Thereafter, individual inserts of the substantially solid treatment composition can be molded or stamped from the polymeric sheet coated with the substantially solid layer of treatment composition and then separated as individual inserts suitable for insertion into a dental tray and placement over a person's teeth. The polymeric sheet may be used as a protective packaging and peeled away prior to inserting the treatment insert into a dental tray.

Alternatively, a flowable or substantially solid dental treatment composition can be directly molded or shaped into an insert. Alternatively, the flowable composition can be cast onto a forming surface and dried to form a substantially solid sheet of treatment composition that is thereafter molded, stamped or otherwise formed into a desired insert shape.

According to another embodiment, the dental treatment composition may be a thermoplastic material. The individual components of the composition may be combined and heated so as to form a flowable liquid or gel composition that is later subsequently cooled to form a substantially solid treatment layer.

The size and shape of solid bleaching or other treatment inserts according to the invention can be tailored to fit into any existing dental tray. For example, the insert may be tailored to be inserted into a dental tray designed to be placed over a person's upper or lower dental arch. They may also be tailored to insert into a dental tray designed to fit persons having differently sized or shaped dental arches. According to one embodiment, the solid bleaching inserts are advantageously designed so as to substantially cover the front and lingual surfaces of the teeth to be bleached. Bleaching both surfaces yields more esthetically appealing teeth. Moreover, bleaching both the front and lingual surfaces helps in bleaching the interproximal spaces between adjacent teeth.

The dental treatment compositions according to the invention have a shape suitable for insertion into a dental tray. The composition may be either flat or contoured, as desired.

According to one embodiment, the dental treatment composition has a horseshoe shape and a U-shaped trough like a conventional bleaching tray. In another embodiment, the treatment insert has an L-shaped profile or "trough". It will be appreciated, however, that treatment inserts according to the invention can have any desired profile or shape.

The dental treatment inserts of the invention can be designed to be worn for any desired time period. Increasing the concentration of dental bleaching or other treatment agent generally reduces the required treatment time. Nevertheless, due to the extremely comfortable fit and reliable adhesion between the insert, dental tray, and the person's teeth, it is possible to maintain such inserts against a person's teeth for extended periods of time in order to ensure even and thorough bleaching or other treatment. Treatment inserts according to the invention can be designed to be worn while, e.g., talking, sleeping, eating, drinking, smiling, frowning, grimacing, yawning, coughing, smoking, or making virtually any facial expression or mouth contortion. This greatly decreases their intrusiveness into everyday activities compared to conventional bleaching strips, which do not reliably adhere to teeth, or intrusive bleaching devices such as large, bulky bleaching dental appliances.

The dental treatment inserts can be designed to be worn for as little as a few minutes or as long as several hours. By way of example, not limitation, a typical bleaching session of fast duration may last from about 10 to about 30 minutes. A bleaching session of intermediate duration may last from about 30 minutes to about 2 hours. A bleaching session of long duration, including professional bleaching or overnight bleaching while a person is sleeping, may last from about 2 hours to about 12 hours. Bleaching sessions may be repeated as many times as are needed to obtain a desired degree of whitening. In some cases, a clinical whitening effect has been observed after only 1–3 whitening sessions. A typical bleaching regimen will preferably include 1–20 bleaching sessions, more preferably 2–15 bleaching sessions, and most preferably 3–10 bleaching sessions.

For convenience of use, multiple inserts and/or dental trays may be packaged together and sold as a kit. In one embodiment, the number of inserts and dental trays provided with each kit can equal the number of sessions that represent a prescribed bleaching regimen. According to another embodiment, the dental trays may be reusable, and the kit may include for example an upper dental tray, a lower dental tray, and a plurality of upper and lower inserts. To efficiently utilize the space within a kit package, multiple inserts and dental trays can be stacked and interested together. The inserts and dental trays can be sealed collectively or individually as desired. The insert may include a removable protective layer over its surface to protect it from contamination or moisture, both of which can possibly cause premature decomposition of the treatment agent (e.g., a peroxide bleaching agent).

The inventive inserts may be used with any dental tray. For example, they may be used with custom trays, non-custom trays, soft and flexible trays, or rigid trays. Such trays may be made from any desired material, for example, but not limited to ethylene-vinyl acetate copolymer (EVA), ethylene-vinyl alcohol copolymer (EVAL), polycaprolactone (PCL), polyvinyl chloride (PVC), polyesters (e.g., polyethylene terephthalate (PET), an example of which is MYLAR), polycarbonates, polyamides, polyurethanes, polyesteramides, polyethylene (PE), high density polyethylene (HDPE), low density polyethylene (LDPE), ultra low density polyethylene (ULDPE), polypropylene (PP), polytetrafluoroethylene (PTFE) (e.g., TEFLON), and mixtures thereof. Plasticizers, flow additives, and fillers known in the art can be used as desired to modify the properties of any of the foregoing polymers used to form a dental tray.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction and Definitions

Figure 1:
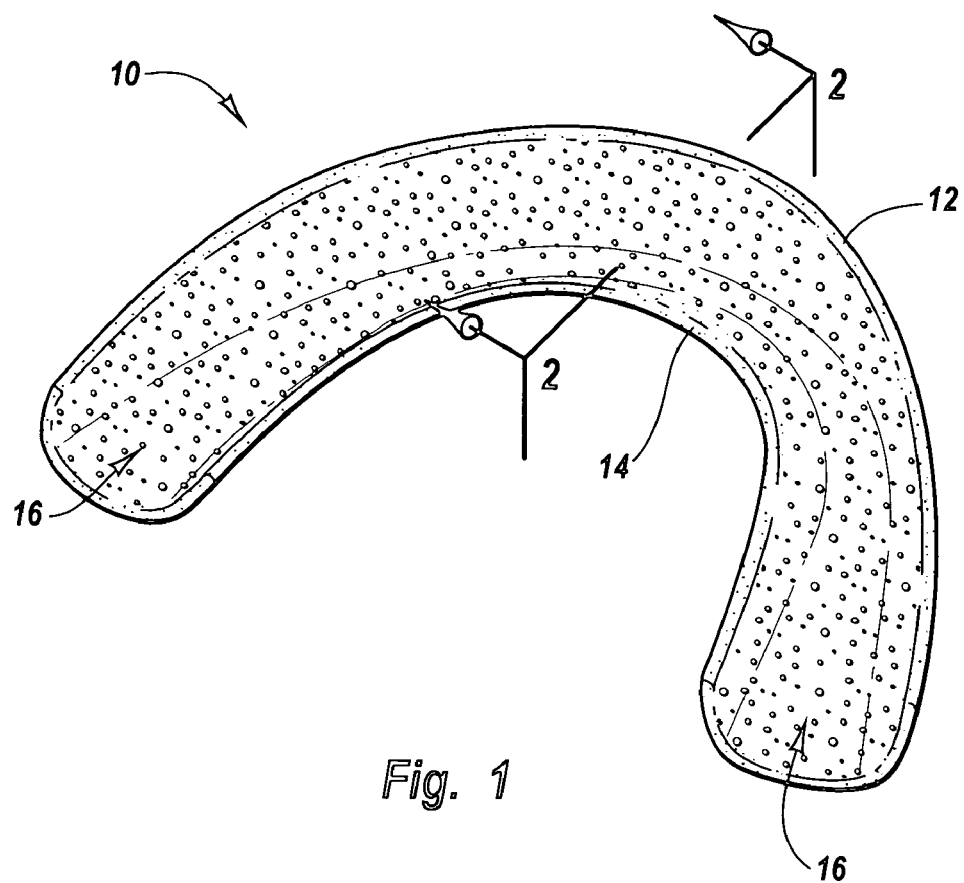
FIG. 1 is a perspective view of an exemplary solid treatment insert according to the invention.

The present invention generally relates to substantially solid bleaching or other treatment compositions in the form of an insert for placement within a dental tray. The substantially solid treatment compositions become more adhesive to teeth when moistened with water or saliva. The treatment inserts easily adhere to a dental tray, and when placed over a person's teeth, the insert reliably adheres to the teeth, maintaining contact between the teeth to be treated (e.g., bleached) and a bleaching or other treatment agent within the treatment composition of the insert.

The term "substantially solid", as used herein, refers to a dental treatment composition that is in a solid or semi-solid condition so that it can be handled and inserted within a dental tray. In one aspect, a "substantially solid" treatment composition can be characterized as a continuous or cohesive mass that does not readily flow or separate when subjected to gravitational forces and which cannot be readily expressed through a syringe outlet or other similarly-sized opening or orifice. Thus, the term "substantially solid" excludes runny bleaching liquids, viscous bleaching liquids, and even thick bleaching gels that are able to flow when subjected to gravity and/or which can be readily expressed through a syringe outlet or other similarly-sized opening or orifice. The term "substantially solid", when used in the context of a treatment composition or layer, also excludes dry particulate bleaching compositions or powders because dry particulates and powders readily flow when subjected to gravity and/or are readily separated (i.e., the particles as a whole have little or no internal cohesion). Moreover, powders or particulates, when viewed as a whole, as not "shaped", coherent, or solid.

One characteristic of "substantially solid" treatment compositions according to the invention is that they become more adhesive when an exposed surface thereof is moistened with, e.g., saliva or water. When moistened, the surface of the treatment composition turns into a sticky material that is able to more strongly adhere to oral tissue (e.g., teeth) compared to a substantially solid treatment composition that has not been moistened. The composition at the surface may become a viscous liquid, paste or gel, at least temporarily, depending on the amount of moisture that is applied to the surface of the "substantially solid" treatment composition. Nevertheless, the consistency of the moistened surface can remain "substantially solid" depending on the degree of initial moistening, or it can stiffen and even revert back to being "substantially solid" as the initial quantity of surface moisture diffuses into a remaining portion of the "substantially solid" treatment composition over time (e.g., during a bleaching procedure in which the bleaching layer or composition is protected from saliva and ambient moisture in a person's mouth by a water-proof dental tray into which the composition is inserted).

The term "dental tray", as used herein, refers to any article of manufacture or device having a tray-like shape so as to facilitate placement of the device or shaped structure over at least a portion of a person's dental arch. A "dental tray" or "tray-like" device includes a front side wall configured to engage front surfaces of a person's teeth when in use, a rear side wall extending laterally from the front side wall, either abruptly by one or more distinct angles or non-abruptly by a curved transition, configured to engage lingual surfaces of the person's teeth, and a trough between said front and rear side walls. A "dental tray" may be configured so that a portion of the front side wall, rear side wall, or a transition portion thereof engages the incisal or occlusal edges of the person's teeth when in use.

The term "trough", as used herein, refers to the region that is at least partially bounded by the front side wall, the rear side wall, and a plane or imaginary curved dome extending from an upper edge of the front side wall and an upper edge of the rear side wall. Thus, a "trough" can theoretically exist whenever the front and rear side walls have a space therebetween and are laterally offset by an angle of less than 180°.

In the case of a trough having a U-shaped or rectangular cross section, at least a portion of the front and rear side walls may be substantially parallel (i.e., be offset by an angle of approximately 0°). In the case of a trough having a V-shaped or trapezoidal cross section, at least a portion of the front and rear side walls may be offset by an acute angle (i.e., by an angle between 0–90°). In the case of a trough having an L-shaped cross section, at least a portion of the front and rear side walls will be offset by an angle centered around approximately 90° (e.g., by an angle in a range of about 70° to about 110°). Thus, a trough having an L-shaped cross section can be a subset or slight variation of a trough having a V-shaped cross section.

The terms "longitudinal", "longitudinal dimension" and "longitudinal profile", as used herein when used to refer to a dental tray or treatment insert, shall refer to the lengthwise dimension of the tray or insert. The tray (and some embodiments of the insert) are horseshoe-shaped or otherwise "longitudinally curved" in the longitudinal dimension so as to approximate the curvature of a person's dental arch, or at least facilitate placement of the tray and insert over the dental arch.

The term "molecular weight", as used herein, refers to number average molecular expressed in Daltons unless otherwise specified.

II. Solid Bleaching or Treatment Inserts

The inventive dental tray inserts comprise a substantially solid treatment composition that becomes more adhesive to teeth when moistened by, e.g., saliva or water. The treatment composition is in the form and shape of a treatment insert intended for placement within a dental tray that protects the treatment composition from excessive ambient moisture within a person's mouth during use. Following are preferred examples of materials and characteristics of bleaching and other treatment compositions according to the invention.

A. Substantially Solid Treatment Compositions

Prior to being moistened in preparation for or during use, the treatment insert comprises a substantially solid and coherent dental treatment composition for placement within a dental tray, as opposed to an amorphous liquid, an amorphous flowable gel, or an amorphous dry powder or particulate bleaching or other treatment composition. Providing a substantially solid and coherent treatment layer better maintains the treatment composition between the dental tray into which the insert is inserted and the teeth being bleached or otherwise treated. This is in contrast to conventional bleaching gels that are loaded into customized or non-customized dental trays or that are applied using bleaching strips, which easily diffuse into the surrounding oral cavity. This, in turn, promotes better tooth whitening (or other treatment) and reduces irritation to surrounding oral tissues and/or at least some of the bad taste normally associated with dental treatments (e.g., dental bleaches).

Substantially solid treatment inserts according to the invention include at least one dental bleaching agent or other treatment agent and at least one oral tissue adhesion agent. In a preferred embodiment, the bleaching or treatment agent is dispersed within a substantially solid matrix comprising the oral tissue adhesion agent. Following are preferred bleaching and other treatment agents and oral tissue adhesion agents.

1. Bleaching Agents

A common dental bleaching agent that is known to bleach teeth and that has been found to be safe for oral use is hydrogen peroxide. However, hydrogen peroxide does not itself exist free in nature, but only as an aqueous solution or as a complex. Preferred dental bleaching agents comprise complexes of hydrogen peroxide because they are more stable than aqueous hydrogen peroxide, which tends to be unstable when heated, especially when water is removed by evaporation.

Non-limiting examples of complexed hydrogen peroxide include carbamide peroxide and metal perborates. Other bleaching agents that can be used to bleach teeth include, but are not limited to, metal percarbonates, peroxides, chlorites, and hypochlorites, peroxy acids, and peroxy acid salts.

Bleaching agents within embodiments of the substantially solid bleaching compositions according to the invention can have any desired concentration, e.g., between 1–90% by weight of the substantially solid dental bleaching composition. The concentration of the dental bleaching agent can be adjusted depending on the intended treatment time for each bleaching session. In general, the shorter the treatment time, the more bleaching agent will be added to accelerate dental bleaching so as to effect bleaching in a shorter time period.

In embodiments of the treatment inserts that include a dental bleaching agent, the one or more bleaching agents are preferably included in an amount in a range of about 5% to about 80% by weight of the substantially solid dental bleaching composition, more preferably in a range of about 10% to about 60% by weight of the substantially solid dental bleaching composition, and most preferably in a range of about 20% to about 50% by weight of the substantially solid dental bleaching composition.

2. Oral Tissue Adhesion Agents

The oral tissue adhesion agent may comprise any known tackifying agent that is substantially non-adhesive or less adhesive, when the dental treatment composition is substantially dry but which becomes more adhesive to oral tissue (e.g., teeth) when the dental treatment composition is moistened with, e.g., water or saliva. A presently preferred oral tissue adhesion agent is polyvinyl pyrrolidone (PVP). In addition, PVP polymers have been found to provide sufficient adhesion to polymer dental trays formed of a wide variety of materials, to be substantially non-adhesive when the dental treatment composition is dry to the touch, and to have superior adhesion to oral tissue when a surface of a substantially solid dental treatment composition is moistened with saliva or water.

Non-limiting examples of polyvinyl pyrrolidone polymers that have been used in formulating treatment compositions according to the invention include Kollidon 30, a polyvinyl pyrrolidone polymer sold by BASF having a molecular weight of 50,000, Kollidon VA 60, a polyvinyl pyrrolidone polymer having a molecular weight of 60,000, and Kollidon 90 F, a polyvinyl pyrrolidone polymer having a molecular weight of 1.3 million. Because PVP polymers having widely varying molecular weights have been found to provide similar adhesion and wetting properties, it is believed that PVP polymers of any molecular weight, at least those having a molecular weight between 50,000 and 1.3 million, will be useful in formulating substantially solid treatment compositions according to the invention.

Other oral tissue adhesion agents that may be used in addition to, or instead of, PVP within the scope of the invention include, but are not limited to, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, PVP-vinyl acetate copolymers, carboxymethylcellulose, carboxypropylcellulose, polysaccharide gums, proteins, and the like.

Although polyethylene oxide polymers comprise a less preferred oral tissue adhesion agent, it has been found that a polyethylene oxide polymer having a molecular weight of 1 million provides better adhesion to polymer materials such as MYLAR than a polyethylene oxide polymer having a molecular weight of 100,000.

The one or more oral tissue adhesion agents are preferably included in an amount in a range of about 10% to about 90% by weight of the substantially solid dental treatment composition (exclusive of any bound water or other solvent), more preferably in a range of about 20% to about 80% by weight of the substantially solid dental treatment composition, and most preferably in a range of about 40% to about 75% by weight of the substantially solid dental treatment composition.

3. Other Components

The substantially solid dental treatment composition may include other components as desired to yield a composition having desired properties. Examples of other components include, but are not limited to, plasticizers and humectants (e.g., glycerin, sorbitol, and polyethylene glycol), volatile solvents (e.g., water and alcohols, such as ethanol), stabilizing agents (e.g., EDTA), neutralizing agents (e.g., sodium hydroxide), thickening agents (e.g., fumed silica), flavorants, sweeteners, and the like.

In addition to or instead of a bleaching agent, the composition may include other treatment agents such as desensitizing agents (e.g., potassium nitrate, other potassium salts, citric acid, citrates, and sodium fluoride), remineralizing agents (e.g., sodium fluoride, stannous fluoride, sodium monofluorophosphate, and other fluoride salts), antimicrobial agents (e.g., chlorhexidine, troclosan, and tetracycline), antiplaque agents, anti-tartar agents (e.g., pyrophosphates salts), or other medicaments.

When water is used as a solvent when manufacturing a substantially solid dental treatment composition according to the invention and then driven off by evaporation to yield a substantially solid composition, it is postulated that a significant amount of water remains bound or associated with the hydrophilic components within the bleaching composition, including the dental bleaching (or other treatment) agent, the oral tissue adhesion agent, and any polyols added as humectants. Although the amount of residual water has not yet been determined, it is believed that approximately 10% of the water added initially remains after the initially flowable dental treatment composition is dried sufficiently to yield a substantially solid treatment composition.

C. Characteristics of Substantially Solid Treatment Compositions and Treatment Inserts Incorporating Such Compositions Dental treatment inserts according to the invention are either flat or contoured in shape. According to a preferred embodiment, the inserts are horseshoe shaped and include a front side wall, a rear side wall, and a trough between the front and rear side walls. Having a horseshoe shape facilitates easy placement of the insert within a dental tray, which can then be placed over a person's teeth.

Dental treatment inserts that have a horseshoe shape and that comprise a substantially solid treatment composition that becomes more adhesive when moistened with water or saliva are easy to insert into a dental tray and then install over a person's teeth. This is especially so when compared with bleaching strips or patches, which are initially flat and which must be manipulated so as to wrap the initially flat strip or patch around the occlusal or incisal edges of the teeth in order to cover the front and lingual tooth surfaces. In addition, the inventive dental treatment compositions and inserts are designed to more reliably adhere and remain in place over the person's teeth compared to conventional bleaching strips, which employ a dental bleaching gel that is already flowable prior to placing the bleaching strip over a person's teeth to be bleached. The result is more effective treatment and better patient compliance. In contrast to conventional bleaching strips, which are not recommended for use while a person eats, drinks, smokes or sleeps, dental treatment compositions and inserts according to the invention can be designed so as to be inserted into a dental tray and worn while talking, sleeping, eating, drinking, smiling, frowning, grimacing, yawning, coughing, smoking, or making virtually any facial expression or mouth contortion.

Figure 2A:
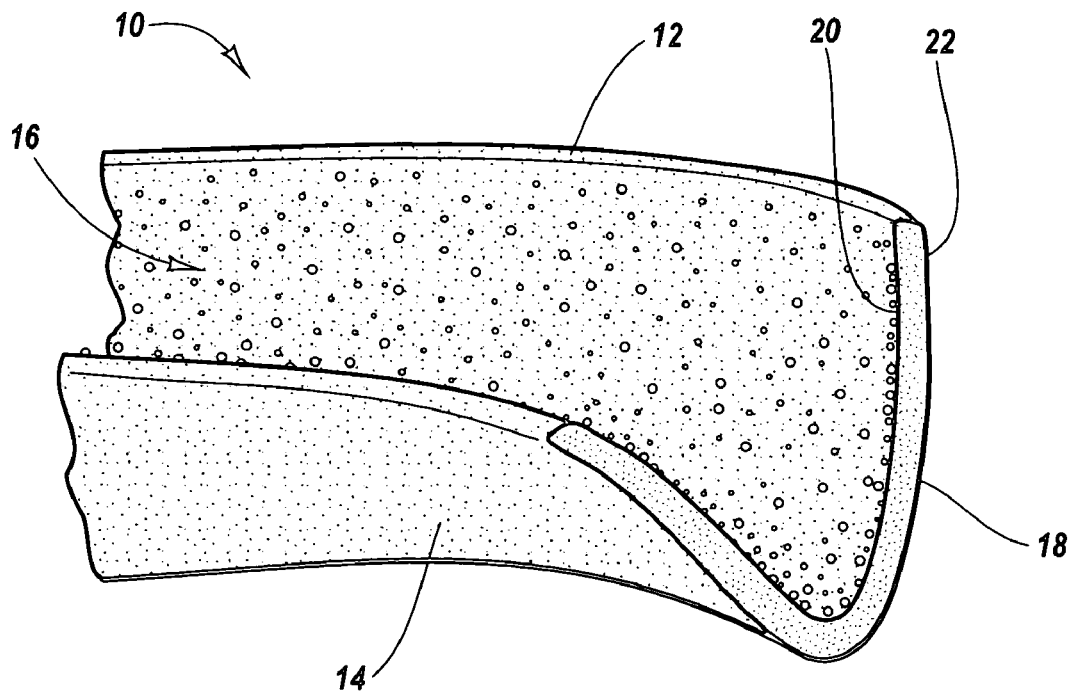
FIG. 2A is a cross-sectional view of the solid treatment insert depicted in FIG. 1.

According to one currently preferred embodiment, the dental treatment insert has a horseshoe shaped longitudinal profile and has a trough with a U-shaped cross section, much like a conventional dental tray. Such a device is depicted in FIGS. 1 and 2. FIG. 1 is a perspective view of a dental treatment insert 10 having a front side wall 12 and a rear side wall 14 that together have a generally horseshoe shape in a longitudinal dimension and that define a trough 16 having a generally U-shaped cross section. The U-shaped cross section of the trough is seen even more clearly in FIG. 2A.

As best seen in FIG. 2A, the treatment insert 10 includes an exterior surface 18 and an interior treatment surface 20 designed to directly contact a person's teeth when the insert 10 is in use. An upper edge 22 of the front side wall can be designed so as to terminate at or shy of the gingival margin of a person's dental arch when in use.

Figure 2B:
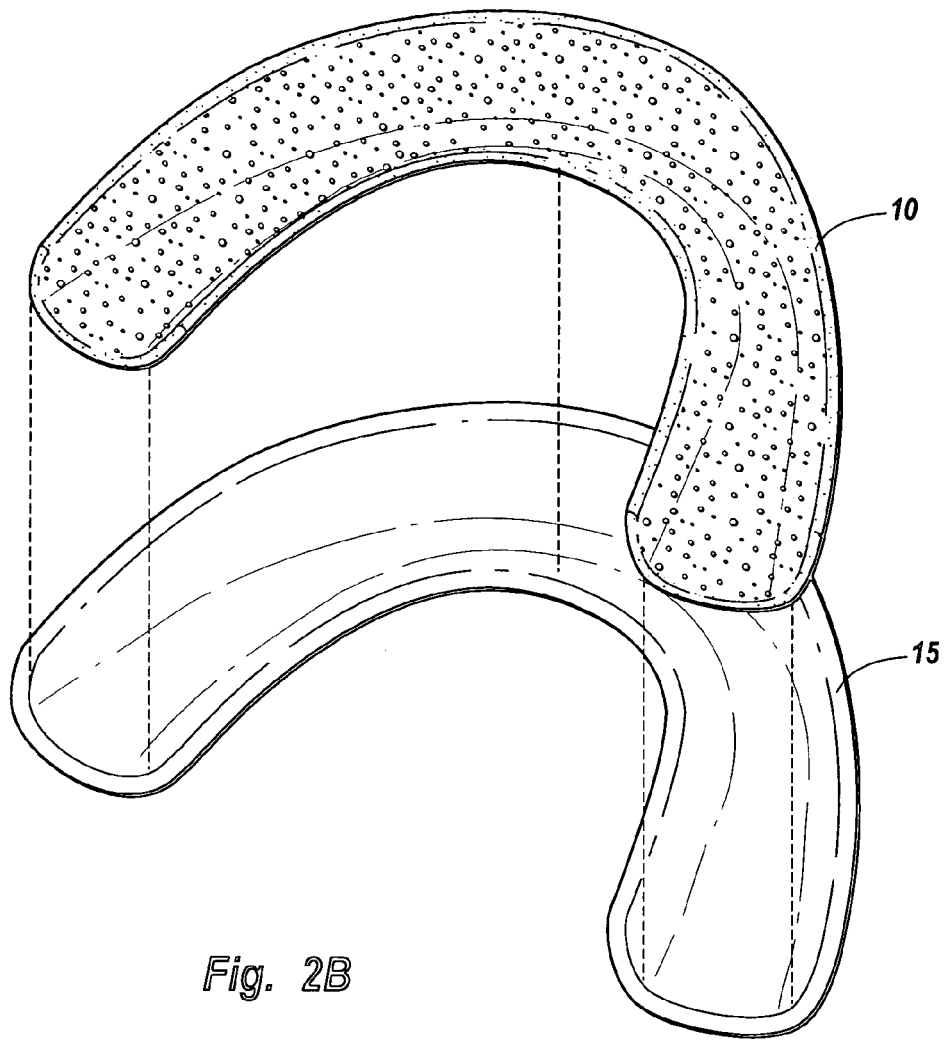
FIG. 2B is an exploded view of the treatment insert of FIG. 1 with a dental tray.
Figure 2C:
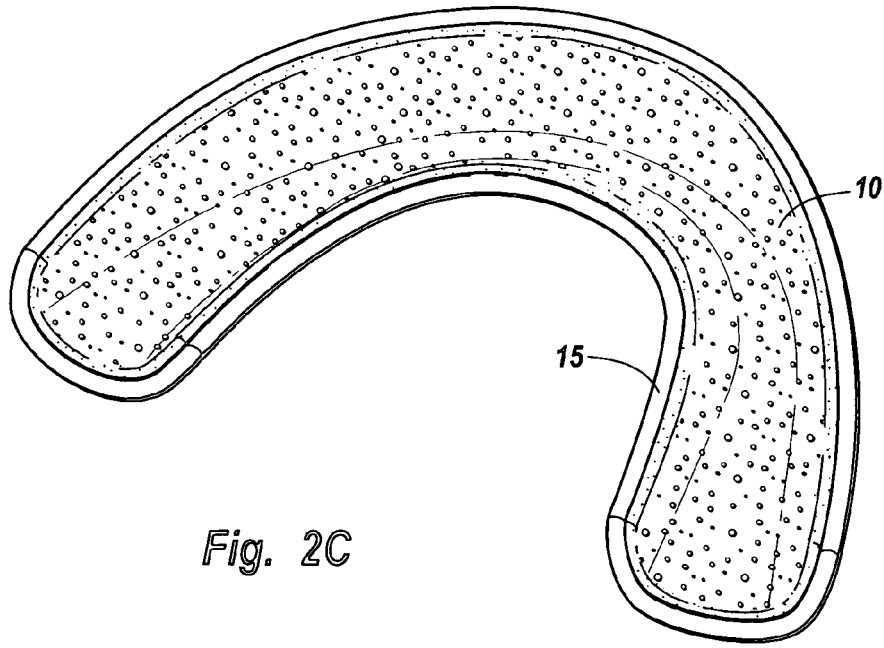
FIG. 2C is a perspective view of the treatment insert and dental tray of FIG. 2B nested together.

The inventive inserts may be used with any dental tray. For example, they may be used with custom trays, non-custom trays, soft and flexible trays, or rigid trays. FIG. 2B illustrates an exploded view of the treatment insert 10 with a dental tray 15. The insert 10 is configured so as to be suitable for placement within dental tray 15. FIG. 2C illustrates the treatment insert 10 nested inside dental tray 15.

Figure 3:
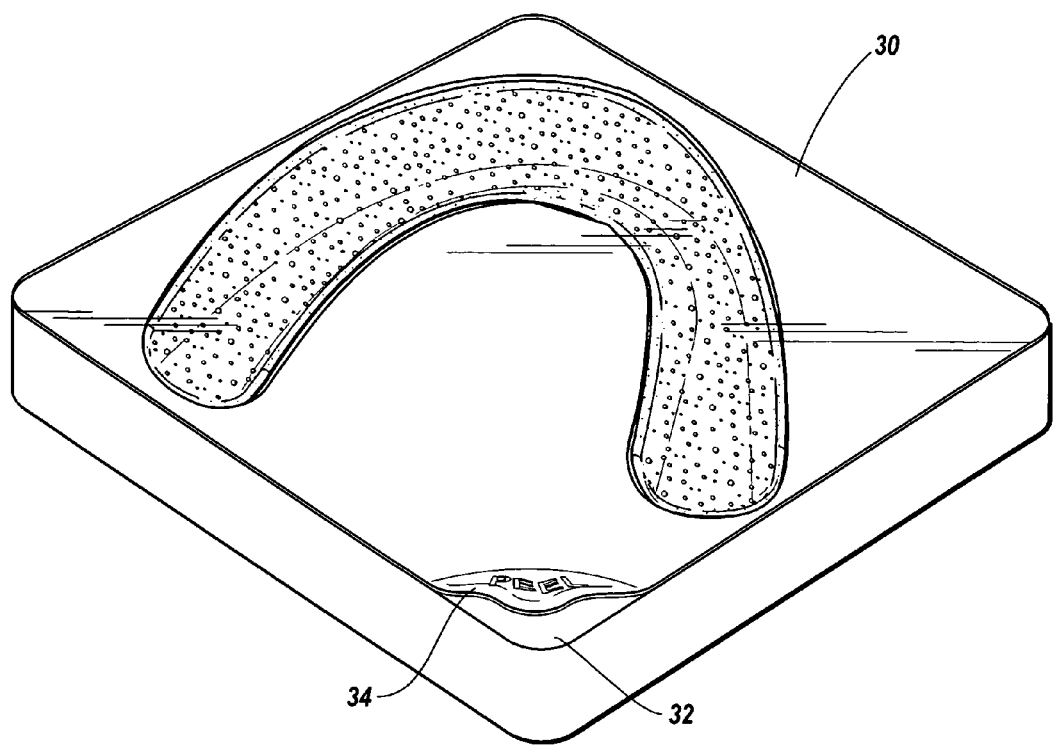
FIG. 3 illustrates the treatment insert of FIG. 1 contained within a sealed protective package having a peelable cover.

In order to protect an insert formed of a substantially solid dental treatment composition from contaminants during storage and prior to use, the insert can be packaged within a sealed container or package. As illustrated in FIG. 3, the insert 10 can be sealed within a protective package 30 that includes a rigid support structure 32 and a peelable cover 34. When it is desired to use the insert 10, the peelable cover 34 is removed and the insert 10 is removed from the support structure 32. In addition to, or instead of, the protective package 30, the insert 10 may alternatively include a removable protective layer (not shown) that is temporarily placed adjacent to at least the interior treatment surface 20 of the treatment insert 10. The removable protective layer may additionally cover the exterior surface 18. When it is desired to use the insert 10, the removable protective layer is removed so as to expose the treatment surfaces 18 and 20.

Figure 4:
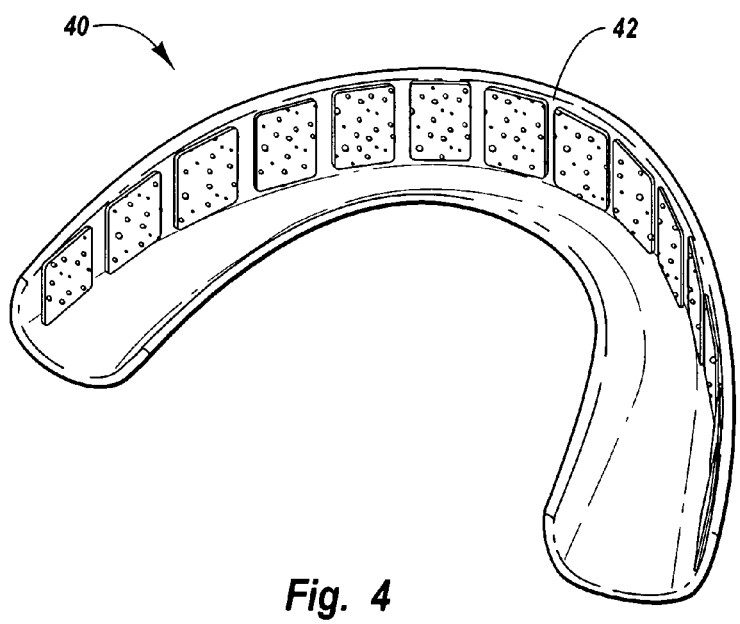
FIG. 4 is a perspective view of a plurality of alternative exemplary solid treatment inserts, each insert positioned as desired in a dental tray so as to allow targeted treatment.

FIG. 4 illustrates a plurality of small inserts 40 that have been inserted into a U-shaped dental tray 42. An insert 40 may be inserted and positioned in the dental tray 42 as desired, so as to allow targeted bleaching of one or more teeth. For example, it may be desirable to position inserts so as to bleach desired teeth while avoiding others. The illustrated inserts 40 are configured to treat the labial surface of the patient's teeth, although other configurations could be configured to treat both the labial and lingual tooth surfaces.

Figure 5:
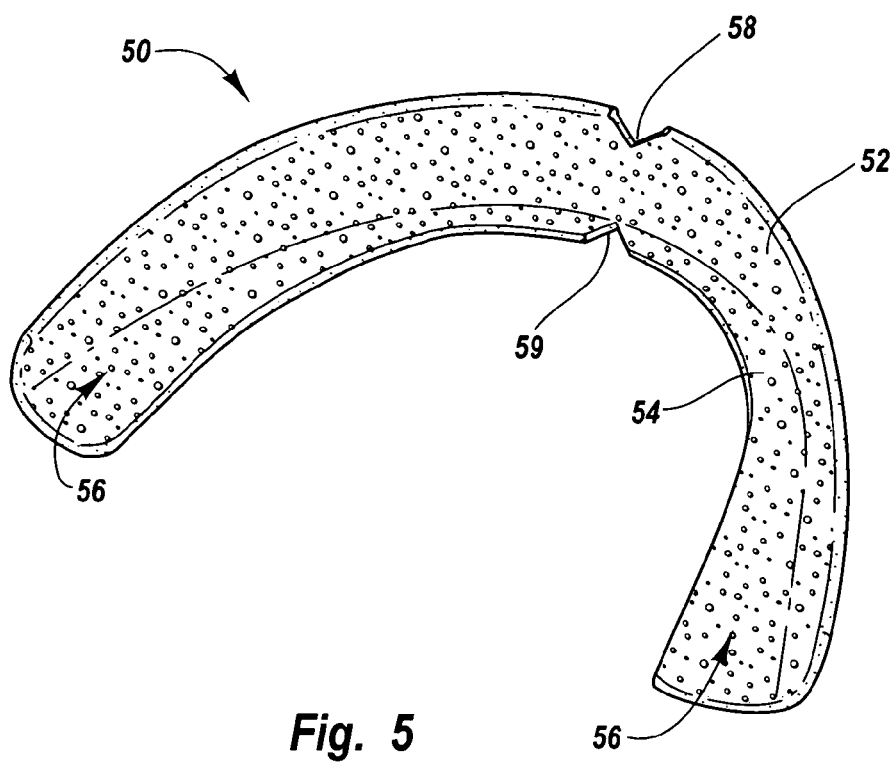
FIG. 5 is a perspective view of an exemplary treatment insert having an L-shaped trough.

FIG. 5 illustrates an alternative embodiment of a treatment insert 50 according to the invention that is L-shaped. More particularly, the insert 50 includes a front side wall 52 and a rear side wall 54 extending laterally from the front side wall 52 so as to form a trough 56 having an approximate L-shaped cross section. The L-shaped insert 50 of FIG. 5 is configured to be inserted into an L-shaped dental tray. L-shaped dental trays and inserts may be somewhat easier to initially place over a person's dental arch compared to U-shaped trays and inserts. This is due to the approximately planar orientation of the rear side wall 54 relative to the occlusal or incisal edges of a person's teeth when the front side wall 52 of the insert 50 is initially placed and adhered against the front surfaces of a person's teeth. On the other hand, more manipulation of an L-shaped insert and tray is generally required to form and adhere to the rear side wall 54 of the insert 50 against the lingual surfaces of the person's teeth as a result of the greater initial offset angle between the front side wall 52 and rear side wall 54. However, the ability of substantially solid dental treatment compositions according to the invention to adhere to oral tissue surfaces almost immediately, or within a few seconds, after being wetted facilitates the process of conforming the front side wall 52 and rear side wall 54 to the person's tooth surfaces.

In the case of the insert 50 having an L-shaped cross section, it may be more correct to say that the rear side wall 54 extending laterally from the front side wall 52 is really a bottom wall rather than a rear side wall. Nevertheless, because this erstwhile "bottom wall" of an L-shaped insert is folded (along with the wall of the dental tray) back against the lingual tooth surfaces during use, it can be readily seen that a treatment insert having an L-shaped trough is merely a variation of an insert having a V-shaped trough. Thus, for purposes of this disclosure and the appended claims, the side wall 54 shall constitute, and fall within the definition of, a "rear side wall".

To facilitate the ability of an insert to conform to the varying shapes and sizes among dental arches, the insert may include mechanical features such as one or more notches within the front or rear side walls. As shown in FIG. 5, the insert 50 includes a notch 58 in an outer edge near the center of the front side wall 52 and a notch 59 in an outer edge near the center of the rear side wall 54. Notches 58 and 59 allow the horseshoe shaped treatment insert to more easily spread open or compress when being conformed to differently-sized dental arches.

Figure 6:
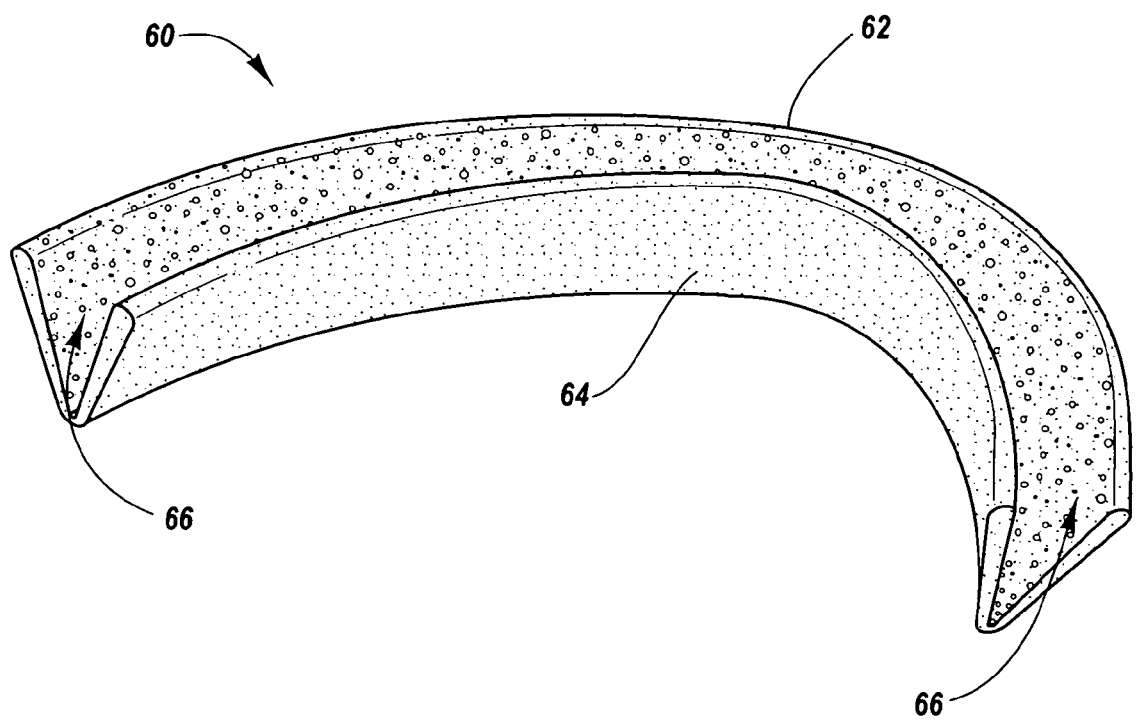
FIG. 6 is a perspective view of an exemplary treatment insert having a V-shaped trough and a curved longitudinal profile

FIG. 6 depicts yet another alternative embodiment of a horseshoe shaped insert 60 according to the invention. The insert 60 includes a front side wall 62 and a rear side wall 64 that define a V-shaped trough 66 and a curved, horseshoe shaped longitudinal profile. The main difference between the V-shaped insert 60 of FIG. 6 and the L-shaped insert 50 of FIG. 5 is the angle at which the front and rear side walls are laterally offset from each other.

Figure 7:
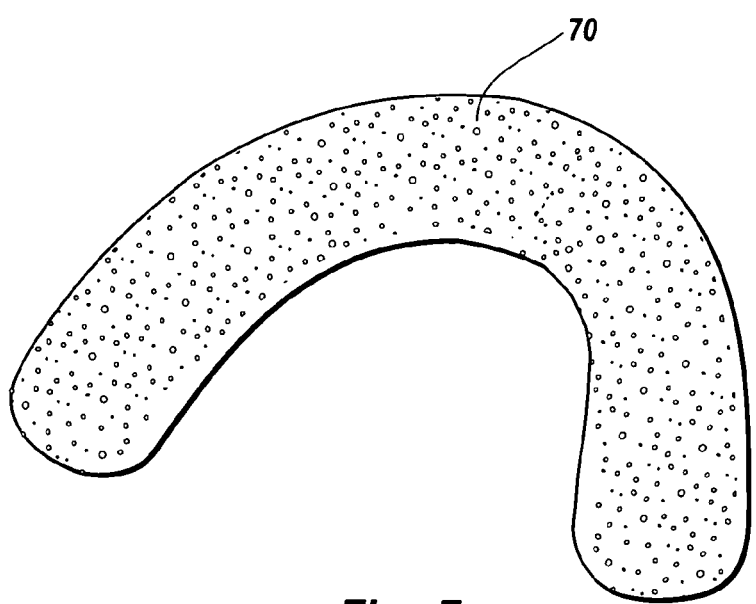
FIG. 7 is a perspective view of an exemplary treatment insert having an initially flat, horseshoe shape.

FIG. 7 illustrates yet another alternative embodiment of a treatment insert 70. Insert 70 is initially substantially flat, rather than contoured. It is horseshoe shaped so as to facilitate placement into a dental tray. As the insert 70 is positioned over the teeth (either before or after insertion into a dental tray) the substantially flat horseshoe profile may be manipulated so as to cover both the lingual and labial surfaces of the teeth to be treated. Because insert 70 is formed of a substantially solid treatment composition, the insert will easily and reliably adhere and remain in place over the person's teeth and within a dental tray once manipulated as desired.

Figure 8:
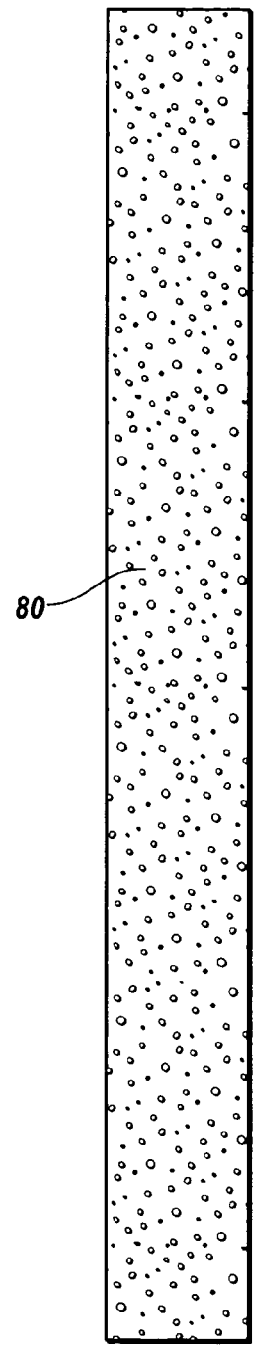
FIG. 8 is a perspective view of an exemplary treatment insert having an initially flat, rectangular shape.

FIG. 8 illustrates yet another alternative embodiment of a treatment insert 80. Insert 80 is initially substantially flat, rather than contoured. It initially includes a rectangular profile, and may be manipulated so as to cover both the lingual and labial surfaces of the teeth. Because insert 80 is formed of a substantially solid treatment composition, the insert will easily and reliably adhere and remain in place over the person's teeth and within a dental tray once manipulated as desired.

Figure 9A:
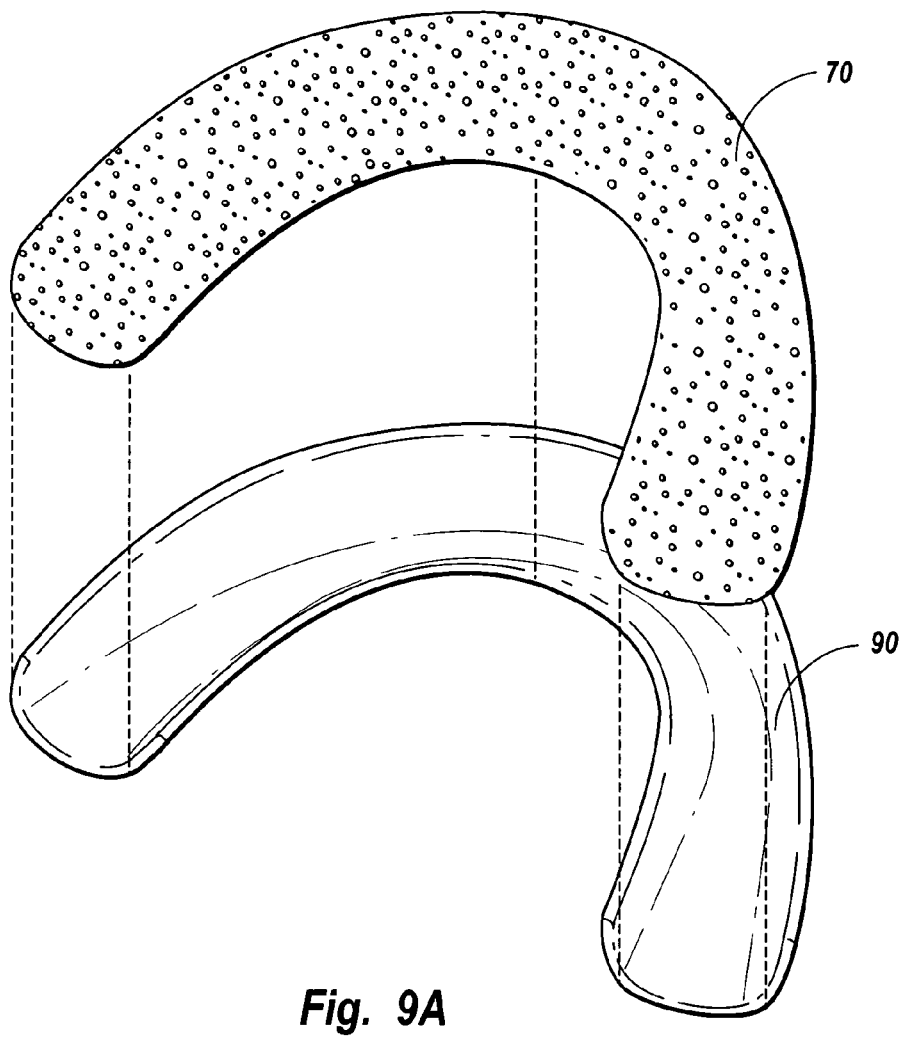
FIG. 9A is an exploded view of the treatment insert of FIG. 7 with a dental tray.
Figure 9B:
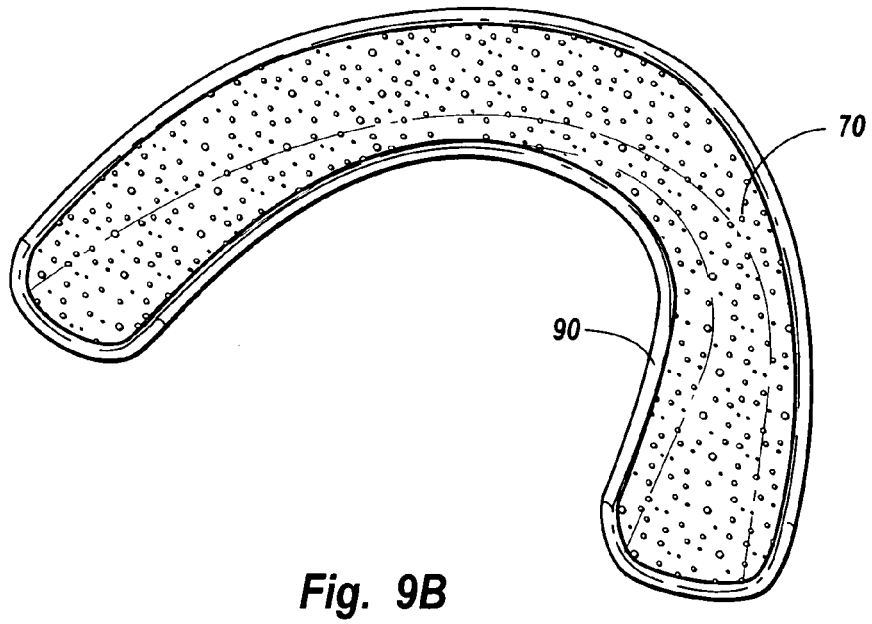
FIG. 9B is a perspective view of the treatment insert and dental tray of FIG. 9A nested together.

FIG. 9A illustrates an exploded view of treatment insert 70 of FIG. 7 with a dental tray 90. The insert 70 is initially substantially flat, rather than contoured. It is horseshoe shaped so as to facilitate placement into a dental tray. As the insert 70 is positioned in the dental tray 90, the substantially flat horseshoe profile may be manipulated so as to nest within the dental tray 90. FIG. 2B illustrates the treatment insert 70 nested inside dental tray 90. In use, treatment insert 70 covers both the lingual and labial surfaces of the teeth to be treated.

Figure 10A:
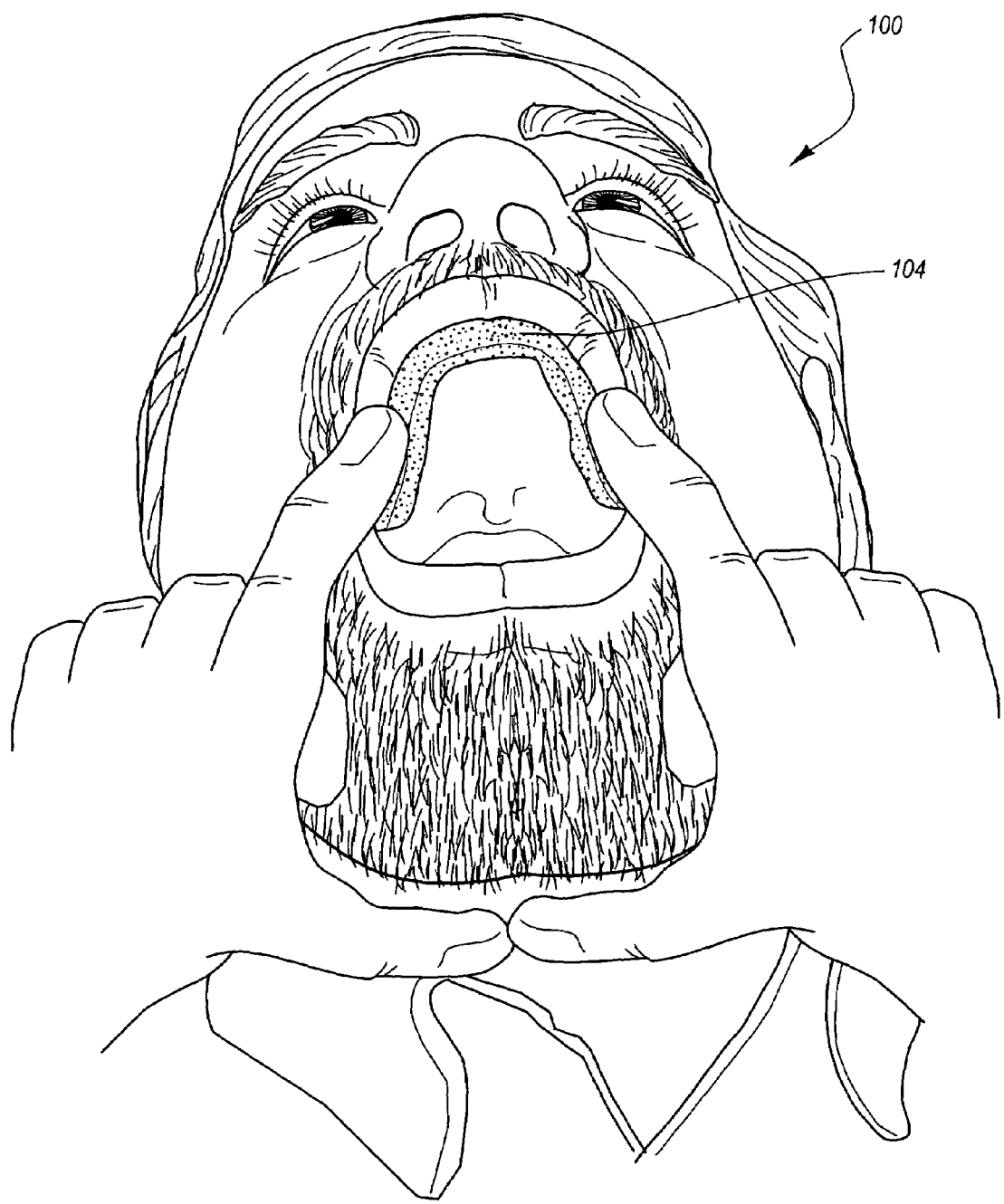
FIG. 10A illustrates a person placing a treatment insert and dental tray over the upper dental arch.
Figure 10B:
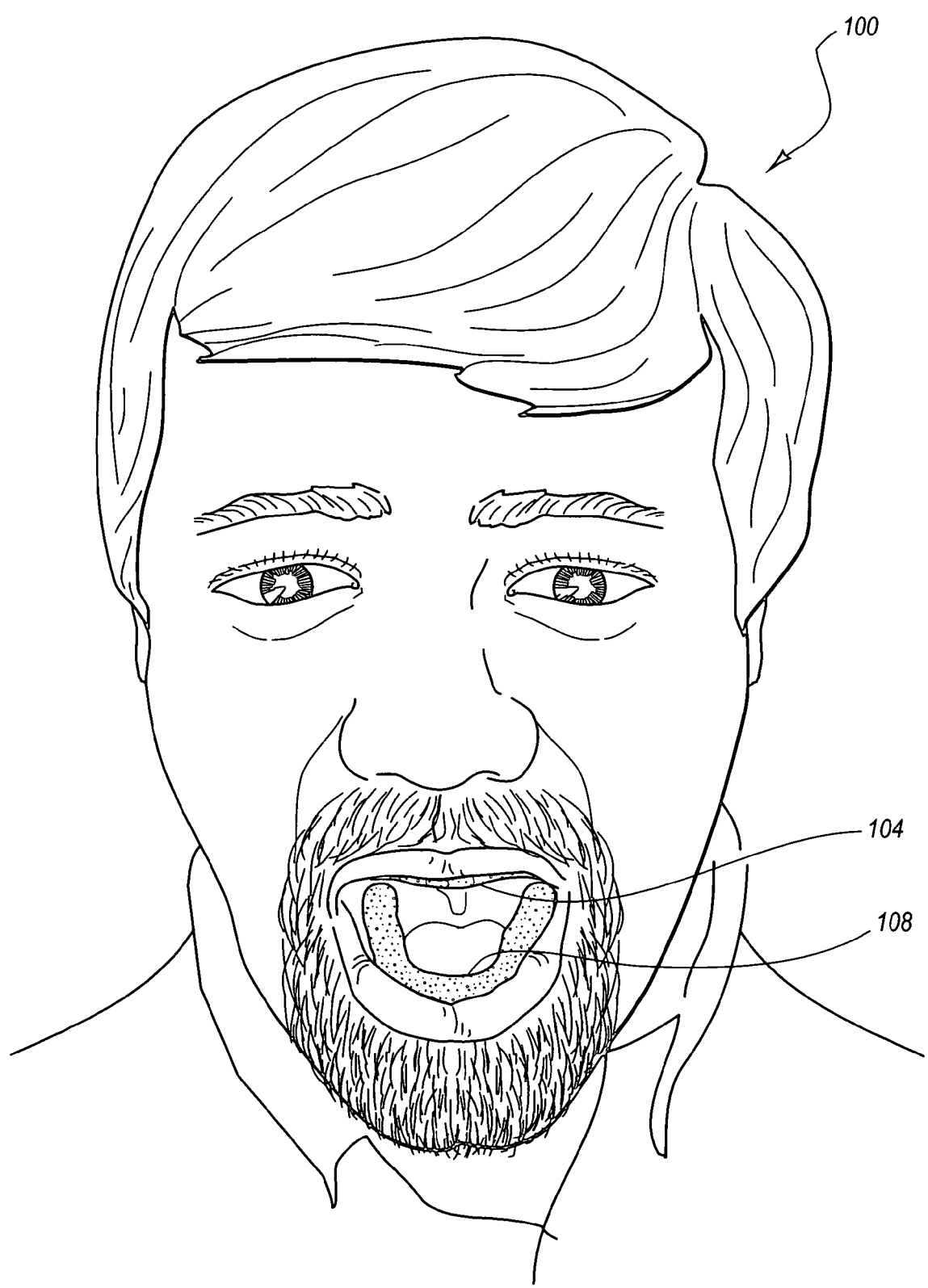
FIG. 10B illustrates a person having placed a treatment insert and dental tray over the lower dental arch, with a treatment insert and dental tray already placed over the upper dental arch.

FIG. 10A illustrates a person 100 placing a dental tray 104 containing a treatment insert disposed therein over the person's upper dental arch. FIG. 10B illustrates the person 100 placing a dental tray 108 containing a treatment insert disposed therein over the person's lower dental arch after having placed the dental tray 104 and associated treatment insert over the upper dental arch. It will be appreciated, however, that the treatment inserts and dental trays can be placed over a person's upper and lower dental arches in any desired order.

The size and shape of dental treatment inserts comprising substantially solid treatment compositions according to the invention can be tailored to more readily fit within any dental tray. For example, they can be sized for trays designed to bleach all or merely a subset of a person's teeth. The inserts may be sufficiently adhesive and flexible so as to readily conform to a wide variety of differently-sized teeth and dental arches. When used for bleaching, the inserts are advantageously designed so as to substantially cover the front and lingual surfaces of the teeth to be bleached. Bleaching both surfaces yields more esthetically appealing teeth, although it is certainly within the scope of the invention to bleach more of one surface than another. Bleaching the front and lingual surfaces helps to bleach the interproximal spaces between adjacent teeth.

In general, the thickness of substantially solid treatment composition of a treatment insert can be adjusted as desired. The treatment insert will generally have a thickness ranging from about 0.1 mm to about 3 mm. One factor affecting the thickness of the treatment insert is the intended duration of each treatment session. In general, increasing the thickness of the composition will provide a longer or more sustained release of active dental treatment agent. By way of example, for short wear times, a treatment insert will preferably have a thickness ranging from about 0.1 mm to about 0.5 mm. For intermediate wear times, the treatment composition insert will preferably have a thickness ranging from about 0.5 mm to about 2 mm. For professional use and for overnight bleaching, the treatment insert will preferably have a thickness ranging from about 2 mm to about 3 mm.

III. Method of Making Substantially Solid Treatment Compositions and Inserts Comprising Such Compositions According to one embodiment, the treatment inserts are made by first forming a flowable treatment composition that is later dried to form a substantially solid treatment composition. This may be performed by heating or otherwise causing one or more volatile solvents to be driven off by evaporation, thus leaving behind a substantially solid treatment composition.

According to one embodiment, the treatment inserts can be made by spreading a flowable dental treatment composition onto the surface of a large or continuous polymeric sheet. The polymeric sheet and treatment composition are then placed into a forced air oven or other appropriate desiccation device in order to heat and drive off a substantial portion of the water or other solvent used to form the flowable dental treatment composition. Removal of the volatile solvent yields a substantially solid treatment composition. Thereafter, individual treatment inserts can be molded, such as by vacuum forming, pressing, or stamping from the coated polymeric sheet, and then separated into individual treatment inserts suitable for use with dental trays and placement over a person's teeth. Alternatively, the substantially solid treatment composition can be separated from the polymeric sheet and then molded, stamped or otherwise formed into a desired shape.

Alternatively, a flowable or substantially solid dental treatment composition can be directly molded or shaped into an insert of a desired shape. Alternatively, the flowable composition can be cast onto a forming surface (e.g., glass) and dried to form a substantially solid sheet of treatment composition that is thereafter molded, stamped or otherwise formed into a desired shape.

IV. Methods of Using Inserts Comprising Substantially Solid Treatment Compositions Dental treatment inserts comprising substantially solid treatment compositions according to the invention can be designed to be placed within a dental tray and Worn for any desired time period. Increasing the concentration of dental bleaching or other treatment agent generally reduces the treatment time required to effect bleaching or other treatment. Nevertheless, due to the extremely comfortable fit and reliable adhesion between the inventive insert and the person's teeth, it is possible to wear an insert placed within a dental tray for extended periods of time in order to ensure more uniform bleaching or other treatment. The inserts may be designed to be inserted into a dental tray and worn while performing normal daily activities, such as talking, eating, drinking, smoking, coughing, smiling, frowning, grimacing, or while sleeping. This greatly decreases their intrusiveness into everyday activities compared to conventional bleaching strips, which do not reliably adhere to teeth, or intrusive bleaching devices such as large, bulky bleaching dental appliances.

Dental treatment inserts according to the invention may be placed within dental trays and worn over a person's upper dental arch, lower dental arch, or both simultaneously. The ability to reliably and comfortably wear the inserts over the upper and lower dental arches simultaneously is another departure from bleaching strips, which are not recommended for use in bleaching the upper and lower dental arches at the same time.

To remove the inserts, a user can pry open a corner of the insert or dental tray into which the insert is placed using a fingernail or rigid tool and then pull the remainder off. Any residual treatment composition that remains adhered to the person's teeth or other oral tissue can be removed by rinsing, and/or by brushing. Although the substantially solid dental treatment compositions are very adhesive to oral tissue when protected from excessive moisture, they can be formulated to quickly break down and dissolve when flushed with excess water and/or by gentle mechanical action (e.g., brushing).

The dental treatment inserts can be worn for as little as a few minutes and as long as several hours. By way of example, not limitation, a typical bleaching session of fast duration may last from about 10 to about 30 minutes. A bleaching session of intermediate duration may last from about 30 minutes to about 2 hours. A bleaching session of long duration, including professional bleaching or overnight bleaching while a person is sleeping, may last from about 2 hours to about 12 hours.

Bleaching sessions may be repeated as many times as are needed to obtain a desired degree of whitening. In some cases, a clinical whitening effect has been observed after only 1–3 whitening sessions. A typical bleaching regimen will preferably include 1–20 bleaching sessions, more preferably 2–15 bleaching sessions, and most preferably 3–10 bleaching sessions.

V. Dental Treatment Kits

For convenience of use, one or more dental bleaching or other treatment inserts may be packaged together with one or more dental trays and sold as a kit. In one embodiment, the number of inserts and dental trays provided with each kit will equal the number of sessions that represent a prescribed bleaching or other treatment regimen. According to another embodiment, the kit includes a number of inserts equal to the number of sessions that represent a prescribed treatment regimen, along with one or more reusable dental trays. Because of the ease of placing the inventive inserts within a dental tray and over a person's teeth, coupled with the reliability with which the inserts adhere to teeth, the likelihood that a particular insert will not work as intended or fail is greatly decreased compared to conventional bleaching strips.

The inventive inserts may be used with any dental tray. For example, they may be used with custom trays, non-custom trays, soft and flexible trays, or rigid trays. Such trays may be made from any desired material, for example, but not limited to ethylene-vinyl acetate copolymer (EVA), ethylene-vinyl alcohol copolymer (EVAL), polycaprolactone (PCL), polyvinyl chloride (PVC), polyesters (e.g., polyethylene terephthalate (PET), an example of which is MYLAR), polycarbonates, polyamides, polyurethanes, polyesteramides, polyethylene (PE), high density polyethylene (HDPE), low density polyethylene (LDPE), ultra low density polyethylene (ULDPE), polypropylene (PP), polytetrafluoroethylene (PTFE) (e.g., TEFLON), and mixtures thereof. Plasticizers, flow additives, and fillers known in the art can be used as desired to modify the properties of any of the foregoing polymers used to form a dental tray.

To efficiently make use of the space within a kit package, multiple inserts and/or dental trays can be stacked or interested together. The inserts and/or dental trays can be sealed collectively or individually as desired. A protective package 30 is depicted in FIG. 3. The inserts may optionally include an additional removable protective layer to protect the treatment composition from contamination or moisture.

VI. Examples of the Preferred Embodiments

The following are several examples of dental bleaching inserts comprising substantially solid dental bleaching compositions that have been formulated and manufactured according to the invention. Such exemplary formulations and manufacturing conditions are given by way of example, and not by limitation, in order to illustrate dental bleaching compositions that have been found to be useful in forming inserts for bleaching a person's teeth. Unless otherwise indicated, all percentages are by weight.

EXAMPLE 1

An initially flowable dental bleaching composition suitable for use in manufacturing a substantially solid, cohesive, and non-flowable treatment composition was formed by mixing together the following components:

| | |
|---|---|
| Carbamide Peroxide | 16% |
| Polyvinyl pyrrolidone (M.W. = 1.3 million) | 38% |
| Water | 46% |

The resulting bleaching composition was spread over the surfaces of three types of flexible polymer sheets: polyethylene sheets, sheets made of paraffin, and MYLAR sheets. The bleaching composition was spread using a spatula. The coated sheets were heated in a forced air oven heated to a temperature of 50–70° C. for approximately 1 hour. The coated sheets were removed from the oven and inspected. The bleaching composition had dried sufficiently so as to form a solid, coherent layer of bleaching composition on the surface of the polymer sheets. The dried bleaching composition adhered well to each of the polymer sheets. The coated sheets were placed back into the oven overnight to remove additional water and to determine whether prolonged heating of the dried composition would cause the carbamide peroxide bleaching agent to decompose.

The coated sheets were removed from the oven a second time, cut apart into smaller-sized pieces, and shaped into inserts suitable for placement into a dental tray over a person's teeth. The horseshoe shaped inserts included front and rear side walls that defined a trough having an approximate U- or V-shaped cross section and were curved in the longitudinal dimension to roughly approximate the horseshoe curvature of the dental trays into which they would be inserted.

The inserts were tested by peeling away the polymer sheet and placing them within a dental tray and then over a person's teeth. The inserts adhered to the dental trays. The residual saliva present on the tooth surfaces moistened the exposed surface of the substantially solid dental bleaching composition and caused it to become sticky and very adhesive to the teeth almost immediately. The dental trays were pressed against the teeth, which caused the inserts to conform to the natural irregularities of the dental arch and adhere firmly against the teeth.

The dental trays and dental bleaching inserts were worn for varying time periods ranging from several minutes to several hours without becoming dislodged. The formation of oxygen bubbles within the moistened bleaching composition against the person's teeth indicated that the peroxide bleaching agent remained active and was suitable for bleaching teeth even after the bleaching composition was heated overnight in an oven. In some cases a noticeable bleaching effect was detected after just one bleaching session (e.g., a 2-hour bleaching session). In all cases, noticeable bleaching was detected after 1–3 bleaching sessions.

In another experiment, the dried substantially solid bleaching composition, when still in the form of a flat sheet, was separated from the polymer sheet and then vacuum formed into a horseshoe shaped insert for placement within a dental tray. This demonstrated that substantially solid bleaching compositions according to the invention can be shaped into a treatment insert independent of a polymer sheet protective layer.

EXAMPLE 2

An initially flowable dental bleaching composition suitable for use in manufacturing a substantially solid, cohesive, and non-flowable dental bleaching composition insert was formed by mixing together the following components:

| | |
|---|---|
| Carbamide Peroxide | 16% |
| PolyOx WSR 101 (M.W. = 1 million) | 7% |
| Water | 77% |

The resulting bleaching gel was spread over the surface of MYLAR sheets using a spatula. The coated sheets were heated in a forced air oven heated to a temperature of 50–70° C. for approximately 1 hour. The coated sheets were removed from the oven and inspected. The bleaching composition had dried sufficiently so as to form a solid, coherent layer of bleaching layer on the surface of the polymer sheets. Unlike the bleaching composition of Example 1, the dried bleaching composition did not adhere strongly to the polymer sheets but was easily separated from the sheets. The coated sheets were placed back into the oven overnight.

The coated sheets were removed from the oven a second time, cut apart into smaller-sized pieces, and formed into horseshoe shaped inserts suitable for insertion into dental trays and subsequent placement over a person's teeth. The inserts included front and rear side walls that defined a trough having an approximate U- or V-shaped cross section and were curved in the longitudinal dimension to roughly approximate the curvature of a dental arch.

The inserts were tested by placing within a dental tray and then over a person's teeth. The residual saliva present on the tooth surfaces moistened the exposed surface of the dry dental bleaching composition and caused it to become sticky and adhesive to teeth within a few seconds. The results of Example 2 indicate that polyethylene oxide was a satisfactory oral tissue adhesion agent.

A substantially solid dental bleaching composition formed from the initially flowable bleaching composition of Example 2 is shaped into a horseshoe shaped insert independently of the polymer sheet.

EXAMPLE 3

An initially flowable dental bleaching composition suitable for use in manufacturing a substantially solid, cohesive, and non-flowable dental bleaching composition was formed by mixing together the following components:

| | |
|---|---|
| Carbamide Peroxide | 16% |
| Carbopol 974P | 5% |
| Aqueous NaOH (50%) | 6% |
| Water | 73% |

The resulting bleaching gel was spread over the surface of MYLAR sheets using a spatula. The coated sheets were heated in a forced air oven heated to a temperature of 50–70° C. for approximately 1 hour. The coated sheets were removed from the oven and inspected. Although the bleaching composition dried sufficiently to form a solid, it shrunk considerably, probably because of the large amount of water that was needed to cause Carbopol to form a gel. Shrinkage of the bleaching composition caused the polymer sheet to become partially shriveled up. Using carboxypolymethylene as an oral tissue adhesion agent resulted in a dried bleaching composition that adhered to the polymer sheet.

Thereafter, the coated sheets were removed from the oven after heating overnight, cut apart into smaller-sized pieces, and formed into horseshoe shaped inserts suitable for insertion into dental trays and subsequent placement over a person's teeth. After removing the polymer sheet protective layer, the insert was placed into the dental tray and over a person's teeth. When placed over a person's teeth it took about 5 seconds for the dental bleaching composition to become moistened enough to start becoming sticky and adhesive to teeth. The insert was able to conform to the person's teeth and remain in place after being pressed against the teeth for about 30–60 seconds.

The results of Example 3 indicate that, while Carbopol 974 P is able to adhere to a MYLAR sheet protective layer and appears to be a satisfactory oral tissue adhesion agent once the bleaching composition is sufficiently moistened, it presents a shrinkage problem that can cause undesirable deformation of thin, flexible polymer sheet protective layers. One would expect Carbopol 974 P to work better when used with less flexible sheets.

A substantially solid dental bleaching composition formed from the initially flowable bleaching composition of Example 3 is shaped into a horseshoe shaped insert independent of a polymer sheet protective layer.

EXAMPLE 4

An initially flowable dental bleaching composition suitable for use in manufacturing a substantially solid, cohesive, and non-flowable dental bleaching composition was formed by mixing together the following components:

| | |
|---|---|
| Polyethylene Oxide (M.W. = 100,000) | 20% |
| Glycerin | 2.5% |
| Sodium Percarbonate | 2.4% |
| Water | 75.1% |

The resulting bleaching gel was spread over the surface of MYLAR sheets as in Example 2. The coated sheets were heated in a forced air oven heated to a temperature of 50–70° C. for approximately 1 hour. The coated sheets were removed from the oven and inspected. The bleaching composition had dried sufficiently so as to form a solid, coherent layer of bleaching layer on the surface of the polymer sheets. When removed from the oven, the bleaching composition of Example 4 did not adhere at all to the MYLAR sheets. This indicates that the lower molecular weight polyethylene oxide of Example 4 was even less adhesive to MYLAR sheets than the higher molecular weight polyethylene oxide of Example 2. Sheets comprising a solid layer of the bleaching composition of Example 2 could also be formed by spreading the composition on a solid surface such as glass, drying the composition, and then peeling off the dried composition.

By comparison, when the bleaching composition of Example 1 was applied to a glass surface and then dried, it adhered so strongly that it could not readily be peeled off the glass surface. Instead, it had to be forcefully chipped or pried off using a razor blade.

Once allowed to sit outside the oven, the bleaching composition of Example 4 did adhere to the MYLAR sheet. Also, the dried bleaching composition of Example 4 did adhere to a person's teeth when moistened, although not as well as the bleaching compositions of Examples 1–3.

A substantially solid dental bleaching composition formed from the initially flowable bleaching composition of Example 4 is shaped into a horseshoe shaped insert independent of a protective polymer sheet.

EXAMPLE 5

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| Water | 25% |
| Ethanol | 25% |
| Polyvinyl pyrrolidone (M.W. = 1.3 million) | 38% |
| Glycerin | 73% |

The resulting bleaching composition was spread over the surfaces of polyethylene, paraffin, and MYLAR sheets as described in Example 1. The coated sheets were heated in a forced air oven heated to a temperature of 50–70° C. for approximately 45 minutes. The coated sheets were removed from the oven and inspected. The bleaching composition had dried sufficiently so as to form a solid, coherent layer of bleaching layer on the surface of the polymer sheets. Using a mixture of water and ethanol as the solvent allowed the bleaching composition to dry in less time than the compositions of Examples 1–4. The inclusion of glycerin helped the bleaching composition remain more flexible and less brittle after drying. The dried bleaching composition adhered well to each of the polymer sheets. After initial drying, the coated sheets were placed back into the oven overnight.

The coated sheets were removed from the oven a second time, cut apart into smaller-sized pieces, and formed into horseshoe shaped inserts suitable for insertion into dental trays and subsequent placement over a person's teeth. The inserts included front and rear side walls that defined a trough having an approximate U- or V-shaped cross section and were curved in the longitudinal dimension to roughly approximate the curvature of a dental arch. The polymer sheet protective layers were peeled away; the inserts were placed within dental trays, and then placed over the teeth. The inserts adhered almost immediately when placed over a person's teeth and caused a noticeable bleaching effect within 1–3 sessions.

A substantially solid dental bleaching composition formed from the initially flowable bleaching composition of Example 5 is shaped into a horseshoe shaped insert independent of a polymer sheet protective layer.

EXAMPLE 6

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| Water | 21% |
| Ethanol | 21% |
| Kollidon VA 64 (M.W. = 60,000) | 40% |
| Carboxy methyl cellulose | 3% |
| PEG 600 | 5% |

Kollidon VA 64 is a polyvinyl pyrrolidone polymer sold by BASF. The resulting bleaching composition was spread over the surfaces of polyethylene, paraffin, and MYLAR sheets as described in Example 1. The coated sheets were heated in a forced air oven heated to a temperature of 50–70° C. for approximately 45 minutes. The coated sheets were removed from the oven and inspected. The bleaching composition had dried sufficiently so as to form a solid, coherent layer of bleaching layer on the surface of the polymer sheets. The inclusion of polyethylene glycol helped the bleaching composition remain more flexible and less brittle after drying. The dried bleaching composition adhered well to each of the polymer sheets. The coated sheets were placed back into the oven overnight.

The coated sheets were removed from the oven a second time, cut apart into smaller-sized pieces, and formed into horseshoe shaped inserts suitable for insertion into dental trays and subsequent placement over a person's teeth. The inserts included front and rear side walls that defined a trough having an approximate U- or V-shaped cross section and were curved in the longitudinal dimension to roughly approximate the curvature of a dental arch. The polymer sheet protective layers were peeled away; the inserts were placed within dental trays, and then placed over the teeth. The inserts adhered almost immediately when placed over a person's teeth and caused a noticeable bleaching effect within 1–3 sessions.

A substantially solid dental bleaching composition formed from the initially flowable bleaching composition of Example 6 is shaped into a horseshoe shaped insert independent of a polymer sheet protective layer.

EXAMPLE 7

An initially flowable dental bleaching composition suitable for use in manufacturing a substantially solid, cohesive, and non-flowable dental bleaching composition was formed by mixing together the following components:

| | |
|---|---|
| Carbamide Peroxide | 11.6% |
| Ethanol | 55.8% |
| Kollidon 90 F (M.W. = 1.3 million) | 24.4% |
| Carboxy methyl cellulose | 2.3% |
| PEG 600 | 5.8% |

The resulting bleaching composition was spread over the surfaces of polyethylene, paraffin, and MYLAR sheets as described in Example 1. The coated sheets were heated in a forced air oven heated to a temperature of 50–70° C. for approximately 30 minutes. The coated sheets were removed from the oven and inspected. The bleaching composition had dried sufficiently so as to form a solid, coherent layer of bleaching layer on the surface of the polymer sheets. Using ethanol as the only solvent allowed the bleaching composition to dry in even less time than the compositions of Examples 5 and 6. The dried bleaching composition adhered well to each of the polymer sheets. The coated sheets were placed back into the oven overnight.

The coated sheets were removed from the oven a second time, cut apart into smaller-sized pieces, and formed into horseshoe shaped inserts suitable for insertion into dental trays and subsequent placement over a person's teeth. The inserts included front and rear side walls that defined a trough having an approximate U- or V-shaped cross section and were curved in the longitudinal dimension to roughly approximate the curvature of a dental arch. The polymer sheet protective layers were peeled away, the inserts were placed within dental trays, and then placed over the teeth.

The inserts adhered almost immediately when placed over a person's teeth and caused a noticeable bleaching effect within 1–3 sessions.

A substantially solid dental bleaching composition formed from the initially flowable bleaching composition of Example 7 is shaped into a horseshoe shaped insert independent of a polymer sheet protective layer.

EXAMPLE 8

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| Ethanol | 65% |
| Kollidon 90 F (M.W. = 1.3 million) | 20% |
| PEG 600 | 5% |

The resulting bleaching composition was spread over the surfaces of polyethylene, paraffin, and MYLAR sheets as described in Example 1. The coated sheets were heated in a forced air oven heated to a temperature of 50–70° C. for approximately 30 minutes. The coated sheets were removed from the oven and inspected. The bleaching composition had dried sufficiently so as to form a solid, coherent layer of bleaching layer on the surface of the polymer sheets. The dried bleaching composition adhered well to each of the polymer sheets. The coated sheets were placed back into the oven overnight.

The coated sheets were removed from the oven a second time, cut apart into smaller-sized pieces, and formed into horseshoe shaped inserts suitable for insertion into dental trays and subsequent placement over a person's teeth. The inserts included front and rear side walls that defined a trough having an approximate U- or V-shaped cross section and were curved in the longitudinal dimension to roughly approximate the curvature of a dental arch. The polymer sheet protective layers were peeled away; the inserts were placed within dental trays, and then placed over the teeth. The inserts adhered almost immediately when placed over a person's teeth and caused a noticeable bleaching effect within 1–3 sessions.

A substantially solid dental bleaching composition formed from the initially flowable bleaching composition of Example 8 is shaped into a horseshoe shaped insert independent of a polymer sheet protective layer.

EXAMPLE 9

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| Ethanol | 64% |
| Kollidon 90 F (M.W. = 1.3 million) | 25% |
| PEG 600 | 1% |

The resulting bleaching composition was spread over the surfaces of polyethylene, paraffin, and MYLAR sheets as described in Example 1. The coated sheets were heated in a forced air oven heated to a temperature of 50–70° C. for approximately 30 minutes. The coated sheets were removed from the oven and inspected. The bleaching composition had dried sufficiently so as to form a solid, coherent layer of bleaching layer on the surface of the polymer sheets. The dried bleaching composition adhered well to each of the polymer sheets. The coated sheets were placed back into the oven overnight.

The coated sheets were removed from the oven a second time, cut apart into smaller-sized pieces, and formed into horseshoe shaped inserts suitable for insertion into dental trays and subsequent placement over a person's teeth. The inserts included front and rear side walls that defined a trough having an approximate U- or V-shaped cross section and were curved in the longitudinal dimension to roughly approximate the curvature of a dental arch. The polymer sheet protective layers were peeled away; the inserts were placed within dental trays, and then placed over the teeth. The inserts adhered almost immediately when placed over a person's teeth and caused a noticeable bleaching effect within 1–3 sessions.

A substantially solid dental bleaching composition formed from the initially flowable bleaching composition of Example 9 is shaped into a horseshoe shaped insert independent of a polymer sheet protective layer.

EXAMPLE 10

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| Ethanol | 64% |
| Kollidon 90 F (M.W. = 1.3 million) | 23% |
| PEG 600 | 1% |
| Aerosil 200 | 2% |

The resulting bleaching composition was spread over the surfaces of polyethylene, paraffin, and MYLAR sheets as described in Example 1. It is believed that the addition of Aerosil 200 acts as a tackifying agent to promote adhesion of the wet bleaching composition to the polymer sheets. The coated sheets were heated in a forced air oven heated to a temperature of 50–70° C. for approximately 30 minutes. The coated sheets were removed from the oven and inspected. The bleaching composition had dried sufficiently so as to form a solid, coherent layer of bleaching layer on the surface of the polymer sheets. The dried bleaching composition adhered well to each of the polymer sheets. The coated sheets were placed back into the oven overnight.

The coated sheets were removed from the oven a second time, cut apart into smaller-sized pieces, and formed into horseshoe shaped inserts suitable for insertion into dental trays and subsequent placement over a person's teeth. The inserts included front and rear side walls that defined a trough having an approximate U- or V-shaped cross section and were curved in the longitudinal dimension to roughly approximate the curvature of a dental arch. The polymer sheet protective layers were peeled away; the inserts were placed within dental trays, and then placed over the teeth. The inserts adhered almost immediately when placed over a person's teeth and caused a noticeable bleaching effect within 1–3 sessions.

A substantially solid dental bleaching composition formed from the initially flowable bleaching composition of Example 10 is shaped into a horseshoe shaped insert independent of a polymer sheet protective layer.

EXAMPLE 11

An initially flowable dental bleaching composition suitable for use in manufacturing a substantially solid, cohesive, and non-flowable dental bleaching composition was formed by mixing together the following components:

| Carbamide Peroxide | 10% |
| --- | --- |
| Ethanol | 66.9% |
| Kollidon 90 F (M.W. = 1.3 million) | 20% |
| PEG 600 | 0.1% |
| Aerosil 200 | 3% |

The resulting bleaching composition was spread over the surfaces of polyethylene, paraffin, and MYLAR sheets as described in Example 1. The coated sheets were heated in a forced air oven heated to a temperature of 50–70° C. for approximately 30 minutes. The coated sheets were removed from the oven and inspected. The bleaching composition had dried sufficiently so as to form a solid, coherent layer of bleaching layer on the surface of the polymer sheets. The dried bleaching composition adhered well to each of the polymer sheets. The coated sheets were placed back into the oven overnight.

The coated sheets were removed from the oven a second time, cut apart into smaller-sized pieces, and formed into horseshoe shaped inserts suitable for insertion into dental trays and subsequent placement over a person's teeth. The inserts included front and rear side walls that defined a trough having an approximate U- or V-shaped cross section and were curved in the longitudinal dimension to roughly approximate the curvature of a dental arch. The polymer sheet protective layers were peeled away; the inserts were placed within dental trays, and then placed over the teeth. The inserts adhered almost immediately when placed over a person's teeth and caused a noticeable bleaching effect within 1–3 sessions.

A substantially solid dental bleaching composition formed from the initially flowable bleaching composition of Example 11 is shaped into a horseshoe shaped insert independent of a polymer sheet protective layer.

EXAMPLE 12

An initially flowable dental bleaching composition suitable for use in manufacturing a substantially solid, cohesive, and non-flowable dental bleaching composition was formed by mixing together the following components:

| Carbamide Peroxide | 10% |
| --- | --- |
| PolyOx (M.W. = 1 million) | 7.5% |
| Water | 75.5% |
| Glycerin | 5% |
| Aerosil 200 | 2% |

The resulting bleaching gel was spread over the surface of MYLAR sheets as in Example 2. The coated sheets were heated in a forced air oven heated to a temperature of 50–70° C. for approximately 1 hour. The coated sheets were removed from the oven and inspected. The bleaching composition had dried sufficiently so as to form a solid, coherent layer of bleaching layer on the surface of the polymer sheets. Upon removal of the bleaching composition from the oven, the bleaching composition of Example 12 did not adhere well to the MYLAR sheets. Once allowed to sit outside the oven, the bleaching composition of Example 12 did adhere to the MYLAR sheets. It also shrunk somewhat after extended drying. The polymer sheet protective layers were peeled away; the inserts were placed within dental trays, and then placed over the teeth. The dried bleaching composition of Example 12 was able to adhere to a person's teeth when moistened.

A substantially solid dental bleaching composition formed from the initially flowable bleaching composition of Example 12 is shaped into a horseshoe shaped insert independent of a polymer sheet protective layer.

EXAMPLE 13

An initially flowable dental bleaching composition suitable for use in manufacturing a substantially solid, cohesive, and non-flowable dental bleaching composition was formed by mixing together the following components:

| Carbamide Peroxide | 10% |
| --- | --- |
| Kollidon 90 F (M.W. = 1.3 million) | 10% |
| Kollidon 30 (M.W. = 50,000) | 20% |
| Water | 53% |
| Glycerin | 5% |
| Aerosil 200 | 2% |

The resulting bleaching composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The bleaching composition had dried sufficiently so as to form a solid, coherent layer of bleaching layer on the surface of the polymer sheets. The dried bleaching composition adhered well to each of the polymer sheets. The coated sheets were placed back into the oven overnight.

The coated sheets were removed from the oven a second time, cut apart into smaller-sized pieces, and formed into horseshoe shaped inserts suitable for insertion into dental trays and subsequent placement over a person's teeth. The inserts included front and rear side walls that defined a trough having an approximate U- or V-shaped cross section and were curved in the longitudinal dimension to roughly approximate the curvature of a dental arch. The polymer sheet protective layers were peeled away; the inserts were placed within dental trays, and then placed over the teeth. The inserts adhered almost immediately when placed over a person's teeth and caused a noticeable bleaching effect within 1–3 sessions.

A substantially solid dental bleaching composition formed from the initially flowable bleaching composition of Example 13 is shaped into a horseshoe shaped insert independent of a polymer sheet protective layer.

EXAMPLE 14

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| Kollidon 90 F (M.W. = 1.3 million) | 27% |
| Water | 50% |
| Glycerin | 7% |
| Aerosil 200 | 6% |

The resulting bleaching composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The bleaching composition had dried sufficiently so as to form a solid, coherent layer of bleaching layer on the surface of the polymer sheets. The dried bleaching composition adhered well to each of the polymer sheets. The coated sheets were placed back into the oven overnight.

The coated sheets were removed from the oven a second time, cut apart into smaller-sized pieces, and formed into horseshoe shaped inserts suitable for insertion into dental trays and subsequent placement over a person's teeth. The inserts included front and rear side walls that defined a trough having an approximate U- or V-shaped cross section and were curved in the longitudinal dimension to roughly approximate the curvature of a dental arch. The polymer sheet protective layers were peeled away; the inserts were placed within dental trays, and then placed over the teeth. The inserts adhered almost immediately when placed over a person's teeth and caused a noticeable bleaching effect within 1–3 sessions.

A substantially solid dental bleaching composition formed from the initially flowable bleaching composition of Example 14 is shaped into a horseshoe shaped insert independent of a polymer sheet protective layer.

EXAMPLE 15

An initially flowable dental bleaching composition suitable for use in manufacturing a substantially solid, cohesive, and non-flowable dental bleaching composition was formed by mixing together the following components:

| | |
|---|---|
| Carbamide Peroxide | 10% |
| Kollidon 90 F (M.W. = 1.3 million) | 28% |
| Water | 50% |
| Glycerin | 7% |
| Aerosil 200 | 5% |

The resulting bleaching composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The bleaching composition had dried sufficiently so as to form a solid, coherent layer of bleaching layer on the surface of the polymer sheets. The dried bleaching composition adhered well to each of the polymer sheets. The coated sheets were placed back into the oven overnight.

The coated sheets were removed from the oven a second time, cut apart into smaller-sized pieces, and formed into horseshoe shaped inserts suitable for insertion into dental trays and subsequent placement over a person's teeth. The inserts included front and rear side walls that defined a trough having an approximate U- or V-shaped cross section and were curved in the longitudinal dimension to roughly approximate the curvature of a dental arch. The polymer sheet protective layers were peeled away; the inserts were placed within dental trays, and then placed over the teeth. The inserts adhered almost immediately when placed over a person's teeth and caused a noticeable bleaching effect within 1–3 sessions.

A substantially solid dental bleaching composition formed from the initially flowable bleaching composition of Example 15 is shaped into a horseshoe shaped insert independent of a polymer sheet protective layer.

EXAMPLE 16

Example 16 illustrates an exemplary thermoplastic composition. A thermoplastic dental bleaching composition suitable for use in manufacturing a substantially solid, cohesive, and non-flowable dental bleaching composition was formed from the following components:

| | |
|---|---|
| Hydrogen Peroxide | 10% |
| PEG 600 | 20% |
| PEG 3350 | 10% |
| PEG 8000 | 20% |
| Water | 10% |
| Glycerin | 20% |
| Polyvinyl pyrrolidone | 10% |

The glycerine and polyethylene glycols were heated to approximately 80° C. to melt them together. After the mix cooled to approximately 50° C., the hydrogen peroxide, water, and polyvinyl pyrrolidone were mixed together, and the solution was added to the glycerine/PEG mixture. The resulting bleaching composition was spread over the surfaces of polyethylene, paraffin, and MYLAR sheets as described in Example 1. The coated sheets were allowed to cool to room temperature, causing the composition to solidify. The coated sheets were inspected. The bleaching composition had set sufficiently so as to form a solid, coherent layer of bleaching layer on the surface of the polymer sheets. The thermoplastic bleaching composition adhered well to each of the polymer sheets.

The coated sheets were cut apart into smaller-sized pieces, and formed into horseshoe shaped inserts suitable for insertion into dental trays and subsequent placement over a person's teeth. The inserts included front and rear side walls that defined a trough having an approximate U- or V-shaped cross section and were curved in the longitudinal dimension to roughly approximate the curvature of a dental arch. The polymer sheet protective layers were peeled away; the inserts were placed within dental trays, and then placed over the teeth. The inserts adhered almost immediately when placed over a person's teeth and caused a noticeable bleaching effect within 1–3 sessions.

A substantially solid dental bleaching composition formed from the initially flowable bleaching composition of Example 16 is shaped into a horseshoe shaped insert independent of a polymer sheet protective layer.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. In an oral treatment system that includes a dental tray and an initially separate bleaching or treatment insert that is insertable by an end user into the dental tray prior to use, a single-layer solid bleaching or treatment insert for placement within a dental tray, comprising:
   a substantially solid and coherent dental treatment composition that is initially separate from the dental tray and is insertable therein while in a dry, unmoistened state, wherein the said composition has increased adhesiveness to teeth when moistened by saliva or water, said composition being either flat or contoured and sufficiently rigid as to maintain its shape absent external support in order to facilitate placement of said insert into a dental tray, said composition including:
      at least one dental bleaching agent or other treatment agent; and
      at least one oral tissue adhesion agent that contributes to or provides increased adhesiveness to oral tissue when said dental treatment composition is moistened by saliva or water.

2. A solid bleaching or treatment insert as recited in claim 1, wherein said composition is initially horseshoe shaped prior to insertion into a dental treatment tray and placement over a person's teeth.

3. A solid bleaching or treatment insert as recited in claim 1, said dental bleaching agent comprising at least one of carbamide peroxide, metal peroxide, percarbonate, perborate, peroxy acid, peroxy acid salt, chlorite, or hypochlorite.

4. A solid bleaching or treatment insert as recited in claim 1, said dental bleaching agent having a concentration in a range of about 5% to about 80% by weight of said dental bleaching composition.

5. A solid bleaching or treatment insert as recited in claim 1, said dental bleaching agent having a concentration in a range of about 10% to about 60% by weight of said dental bleaching composition.

6. A solid bleaching or treatment insert as recited in claim 1, said dental bleaching agent having a concentration in a range of about 20% to about 50% by weight of said dental bleaching composition.

7. A solid bleaching or treatment insert as recited in claim 1, said oral tissue adhesion agent comprising polyvinyl pyrrolidone.

8. A solid bleaching or treatment insert as recited in claim 1, said oral tissue adhesion agent comprising at least one of carboxypolymethylene, polyethylene oxide, polyacrylic acid, copolymer of polyacrylic acid, polyacrylate, polyacrylamide, copolymer of polyacrylic acid and polyacrylamide, PVP-vinyl acetate copolymer, carboxymethylcellulose, carboxypropylcellulose, polysaccharide gum, protein.

9. A solid bleaching or treatment insert as recited in claim 1, said oral tissue adhesion agent having a concentration in a range of about 10% to about 90% by weight of said dental bleaching composition.

10. A solid bleaching or treatment insert as recited in claim 1, said oral tissue adhesion agent having a concentration in a range of about 20% to about 80% by weight of said dental bleaching composition.

11. A solid bleaching or treatment insert as recited in claim 1, said oral tissue adhesion agent having a concentration in a range of about 40% to about 75% by weight of said dental bleaching composition.

12. A solid bleaching or treatment insert as recited in claim 1, said dental treatment composition further comprising at least one humectant.

13. A solid bleaching or treatment insert as recited in claim 1, said other treatment agent comprising at least one of a desensitizing agent, a remineralizing agent, an antimicrobial agent, an anti-plaque agent, an anti-tartar agent, or another medicament.

14. A kit for use in bleaching or otherwise treating a person's teeth comprising a plurality of single-layer bleaching or treatment inserts that are initially separate from and insertable by an end user into a dental tray, each bleaching or treatment insert comprising:
   a substantially solid and coherent dental treatment composition that is initially separate from the dental tray and is insertable therein while in a dry, unmoistened state, wherein the said composition has increased adhesiveness to teeth when moistened by saliva or water, said composition being either flat or contoured and sufficiently rigid as to maintain its shape absent external support in order to facilitate placement of said insert into a dental tray, said composition including:
      at least one dental bleaching agent or other treatment agent; and
      at least one oral tissue adhesion agent that contributes to or provides increased adhesiveness to oral tissue when said dental treatment composition is moistened by saliva or water.

15. A kit as recited in claim 14, further comprising one or more dental trays that are initially separate from the bleaching or treatment inserts.

16. A kit as defined in claim 15, wherein said kit includes from 3 to 10 bleaching or treatment inserts and 3 to 10 dental trays.

17. A kit as defined in claim 15, wherein said one or more dental trays comprise one or more customized trays, non-custom trays, flexible trays, or rigid trays.

18. A method of using a bleaching or treatment insert to bleach or treat a person's teeth, comprising:
   (a) providing a bleaching or treatment insert, said bleaching or treatment insert comprising:
      a substantially solid and coherent dental treatment composition that has increased adhesiveness to teeth when moistened by saliva or water, the composition being either flat or contoured, the composition including:
         at least one dental bleaching agent or other treatment agent; and
         at least one oral tissue adhesion agent that contributes to or provides increased adhesiveness to oral tissue when said dental treatment composition is moistened by saliva or water;
   (b) providing a dental tray that is initially separate from the bleaching or treatment insert;
   (c) the person placing said bleaching or treatment insert into said dental tray;
   (d) moistening an exposed surface of said substantially solid dental treatment composition so as to increase adhesiveness of said dental treatment composition to teeth prior to placing said bleaching or treatment insert over at least a portion of the person's teeth; and
   (e) placing said bleaching or treatment insert and dental tray over at least a portion of the person's teeth for a desired time period, the substantially solid dental treatment composition of said bleaching or treatment insert adhering and retaining said bleaching or treatment insert against the person's teeth during the desired time period.

19. A method as recited in claim 18, wherein moistening an exposed surface of the substantially solid dental treatment composition is performed by allowing residual saliva on the person's teeth to moisten the exposed surface as said bleaching or treatment insert is placed over the person's teeth.

20. A method as recited in claim 18, wherein moistening an exposed surface of said substantially solid dental treatment composition is performed by applying water or an aqueous solution to the exposed surface.

21. A method as recited in claim 18, further comprising removing said dental tray and said bleaching or treatment insert.

22. A method as recited in claim 21, said dental tray and said bleaching or treatment insert being removed about 10 to about 30 minutes after being placed over the person's teeth.

23. A method as recited in claim 21, said dental tray and said bleaching or treatment insert being removed about 30 minutes to about 2 hours after being placed over the person's teeth.

24. A method as recited in claim 21, said dental tray and said bleaching or treatment insert being removed about 2 hours to about 12 hours after being placed over the person's teeth.

* * * * *

UNITED STATES PATENT AND TRADEMARK OFFICE
CERTIFICATE OF CORRECTION

PATENT NO. : 7,172,423 B2
APPLICATION NO. : 10/888041
DATED : February 6, 2007
INVENTOR(S) : Allred et al.

It is certified that error appears in the above-identified patent and that said Letters Patent is hereby corrected as shown below:

Column 5
Line 47, change "interested" to --internested--

Column 6
Line 39, after "profile", insert --;--

Column 11
Line 54, change "40" to --42--
Line 55, change "42" to --40--
Line 55, change "40" to --42--
Line 56, change "42" to --40--
Line 60, change "40" to --42--

Column 14
Line 27, change "Worn" to --worn--

Column 19
Line 13-14, change percent composition of glycerin from "73%" to --2%--

Signed and Sealed this

Twenty-second Day of July, 2008

JON W. DUDAS
*Director of the United States Patent and Trademark Office*